(12) United States Patent
Ho

(10) Patent No.: US 9,119,758 B2
(45) Date of Patent: Sep. 1, 2015

(54) LIP ENHANCEMENT AND ENLARGEMENT DEVICE

(76) Inventor: Thienna Ho, San Francisco, CA (US)

(*) Notice: Subject to any disclaimer, the term of this patent is extended or adjusted under 35 U.S.C. 154(b) by 521 days.

(21) Appl. No.: 13/586,758

(22) Filed: Aug. 15, 2012

(65) Prior Publication Data

US 2013/0046211 A1 Feb. 21, 2013

Related U.S. Application Data

(60) Provisional application No. 61/524,157, filed on Aug. 16, 2011.

(51) Int. Cl.
*A61H 9/00* (2006.01)
*A61M 1/08* (2006.01)

(52) U.S. Cl.
CPC ...... *A61H 9/0057* (2013.01); *A61H 2201/0153* (2013.01); *A61H 2205/022* (2013.01); *A61M 1/08* (2013.01)

(58) Field of Classification Search
CPC ............... A61H 7/00–7/008; A61H 2007/009; A61H 9/0058; A61H 2009/0064; A61H 2205/022
See application file for complete search history.

(56) References Cited

U.S. PATENT DOCUMENTS

| 1,983,601 | A | * | 12/1934 | Conn | 604/22 |
| 2,441,868 | A | * | 5/1948 | Casnati | 601/6 |
| 3,068,868 | A | | 12/1962 | Skopyk | |
| 3,742,607 | A | * | 7/1973 | Johnson | 433/91 |
| 5,695,445 | A | | 12/1997 | Khouri | |
| 5,871,456 | A | | 2/1999 | Armstrong et al. | |
| 5,897,512 | A | * | 4/1999 | Zagame | 601/6 |
| 6,196,982 | B1 | * | 3/2001 | Ball | 601/6 |
| 8,858,472 | B2 | * | 10/2014 | Gomez | 601/6 |
| 2004/0073144 | A1 | * | 4/2004 | Carava | 601/6 |
| 2004/0254588 | A1 | * | 12/2004 | Kim | 606/131 |
| 2005/0147578 | A1 | | 7/2005 | Menon et al. | |
| 2006/0155219 | A1 | * | 7/2006 | Potter | 601/11 |
| 2006/0235339 | A1 | * | 10/2006 | Naldoni | 601/2 |
| 2007/0016277 | A1 | | 1/2007 | Karat et al. | |
| 2009/0030368 | A1 | * | 1/2009 | Silver | 604/74 |
| 2009/0217931 | A1 | | 9/2009 | Davies et al. | |
| 2010/0137256 | A1 | * | 6/2010 | Haddad | 514/114 |
| 2011/0082391 | A1 | | 4/2011 | Kane et al. | |

(Continued)

FOREIGN PATENT DOCUMENTS

KR 2009-0069590 A 7/2009
WO 2010062292 A1 6/2010

OTHER PUBLICATIONS

U.S. Appl. No. 12/474,920 entitled "Full Lips Self Suction Device and Process Therefore," filed May 29, 2009.

(Continued)

*Primary Examiner* — Valerie L Skorupa
(74) *Attorney, Agent, or Firm* — Jonathan Jaech; Snell & Wilmer L.L.P.

(57) ABSTRACT

A lip enhancement and enlargement device includes a suction element and a lip shaper coupled to the suction element. Each type of lip shaper includes one or more features that allow the device to shape and contour lips. A lip shaper may include one or more contouring elements that change the shape of an upper lip, for example. A lip shaper may also include shaping and contouring elements that form a fuller, unitary lip lobe or two fuller, lip lobes. Lip enhancement and enlargement kits and methods are also disclosed.

4 Claims, 29 Drawing Sheets

(56) References Cited

U.S. PATENT DOCUMENTS

2011/0313412 A1* 12/2011 Kim et al. .................. 606/33
2012/0150079 A1* 6/2012 Rosenberg .................. 601/6

OTHER PUBLICATIONS

International Search Report and Written Opinion mailed on Feb. 1, 2013, total 6 pages.

Nov. 3, 2010, "Luscious Lips", Related Art from website: http://web.archive.org_cynthiarowland_dot_com_lips_exercise.

Jun. 28, 2011, "Lip Plumping", Related Art from website: http://web.archive.org/web/20110628192917/http:/www.lipplumpingshop.com/.

Dec. 14, 2010, "Jolie Lips, Lip Plumper—CosmeSearch, Inc.", Related Art from website: http://web.archive.org/web/20101214202333/http://cosmesearch.com/jolielips/index.html.

Oct. 16, 2010, "Lip pump or plumper for very thin lips", Essentials website:http://www.essentialdayspa.com/forum/viewthread.php?tid=39939.

Aug. 19, 2009, "Two products I have road tested & want to share", Essentials website: http://www.essentialdayspa.com/forum/viewthread.php?tid=35209.

\* cited by examiner

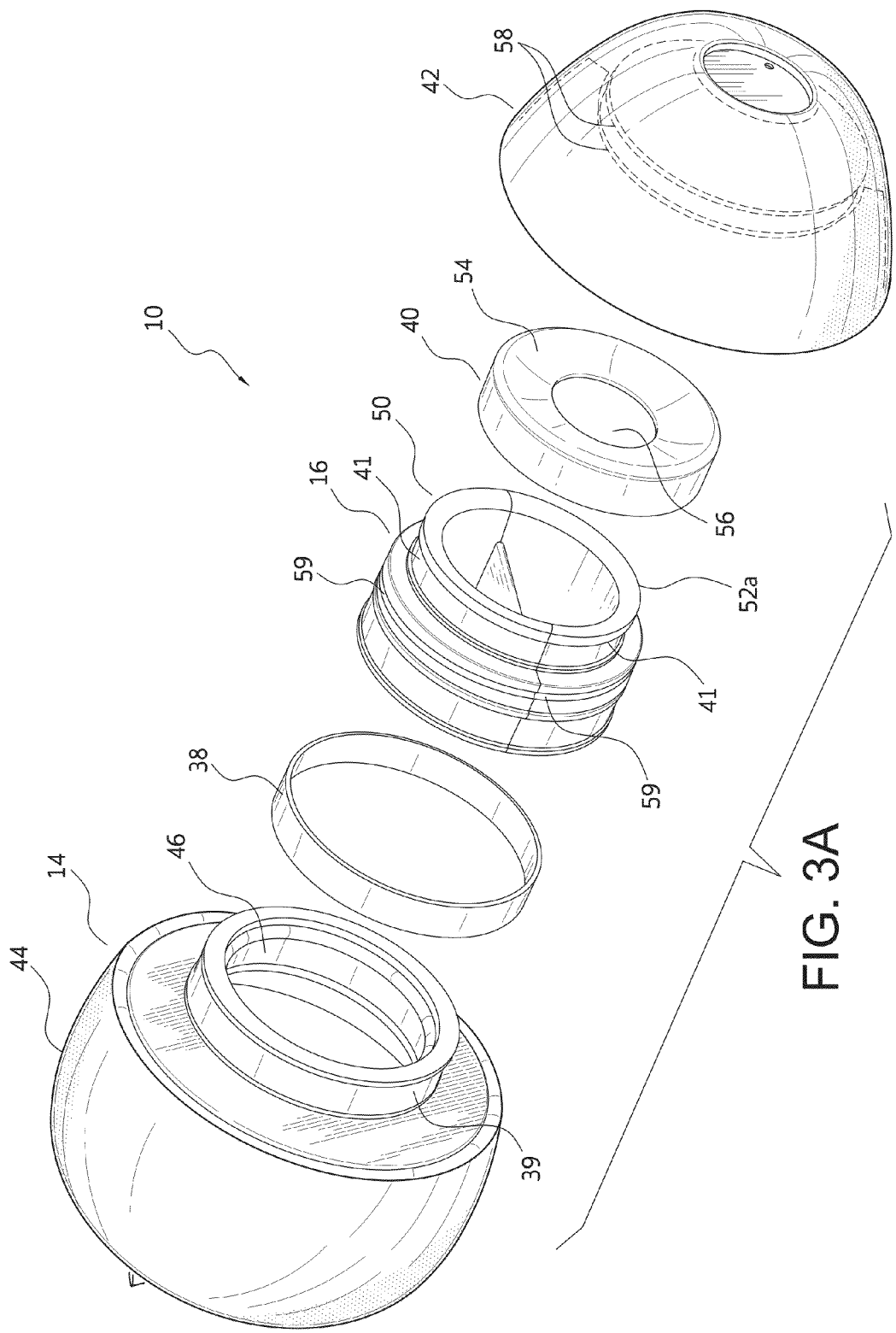

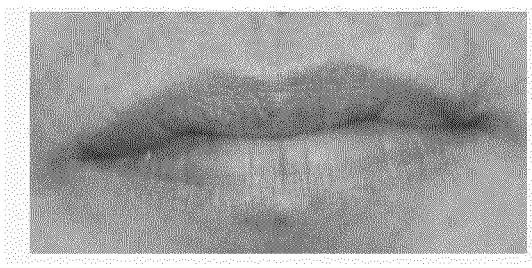 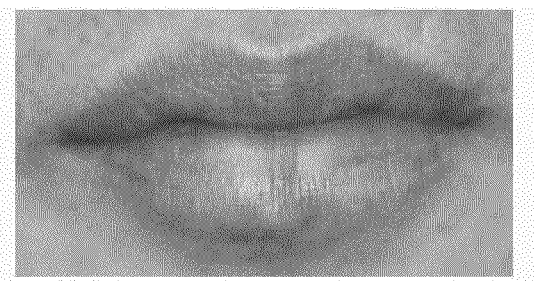
FIG. 27A  FIG. 27B
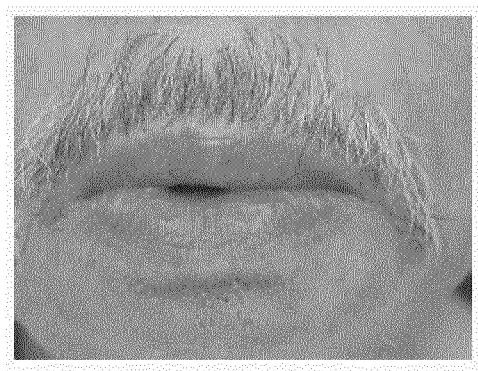 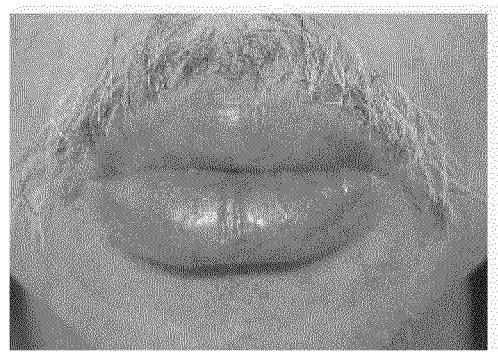
FIG. 28A  FIG. 28B

LIP ENHANCEMENT AND ENLARGEMENT DEVICE

CROSS-REFERENCE TO RELATED APPLICATION

This application claims priority under 35 U.S.C. §119(e) to U.S. Application Ser. No. 61/524,157, filed Aug. 16, 2011, the entirety of which is incorporated herein by reference.

BACKGROUND OF THE INVENTION

1. Field

The present disclosure relates to lip enhancement and enlargement devices, kits, and methods.

2. Background

Lip size and shape are facial features, which directly impact attractiveness levels. Many believe a person's lips and smile to be an indicator of beauty. Full lips, especially in Western cultures, are considered attractive. Some suggest that the trend towards fuller lips developed because lips become less full with age. As one ages, gravitational effects and atrophy of tissue and muscles on and surrounding the lips often lead to lips which appear deflated and disproportionate. Fuller lips, however, are often associated with a healthy lifestyle, youth, and beauty.

In one study, it was found that men give more attention to women with fuller lips. Women having "luscious pouts" were found to attract more attention from men compared to thin-lipped women. In this same study, lips were found to represent one of the most sensual areas on a woman's body and serve as a biological indicator of a woman's health and fertility.

Because of the trend toward fuller lips, many go to considerable lengths to enhance lip shape and size. Therefore, several procedures and devices have been developed to enlarge lips and change lip shape. Lip augmentation, for example, is used frequently in surgical and non-surgical procedures to increase lip fullness. These procedures include injecting and implanting various types of materials into the lips.

But, many risks are associated with lip augmentation. Lips can be overfilled with injected materials. Allergic reactions to anesthetics and injected and implanted materials can occur, resulting in redness, swelling, itching, etc. Abnormal lip shapes may develop, e.g. trout pout, duck lips, sausage lips, fish lips, etc. Bruising and scarring may occur at injection and surgical sites. Implants may move and/or break through skin. Nonetheless, many are still willing to bear these risks.

In addition to these known risks, lip augmentation is considered extremely expensive by many. Costs for an injection can easily range from five hundred to one thousand dollars (US$). Because lip fullness will decrease over time, additional sessions—totaling multiple thousands of dollars—may be required to maintain fuller lips.

Because of the multitude of risks associated with lip augmentation, some have turned to using a nonsurgical device, commonly known as a lip pump, to increase lip size. These types of lip enlargement devices use some form of suction, i.e. negative pressure, applied over both lips to increase blood flow and cause lip size to temporarily increase. Although useful for their intended purpose, currently available lip pumps can have negative side effects. After use, some lip pumps will leave unattractive marks, bruising, indentations, and grooves around a user's lip area. In addition, some lip pumps continuously apply suction to both lips. Unfortunately, these types of lip pumps can cause misshaped lips and fail to address various lip problems. A user who only wants to increase a smaller lower lip, for example, may come away with a "ducky" upper lip that appears similar to a duck bill.

Considering the limitations of known lip pumps and the numerous risks associated with lip augmentation, the need for improved lip enhancement and enlargement devices is clear. The present invention fulfills this need and provides further related advantages, as described in the following summary.

SUMMARY

Each type of lip enhancement and enlargement device disclosed herein includes a suction element and at least one lip shaper coupled to the suction element. A lip shaper may, however, be included in a lip shaper assembly having one or more shapers, specific to the upper and/or lower lips or sections of the upper and/or lower lips. Each lip shaper, however, includes features that allow the lip enhancement and enlargement device to shape and contour a user's lips.

A lip shaper may include one or more contouring elements that change the shape of a user's lip(s). Various types of lip shapers may be included in the lip shaper assembly, depending on the shaping and contouring desired by a user. One type of lower lip shaper may be configured to form a fuller, unitary lower lip lobe, while another type of lip shaper may be configured to form two fuller, lower lip lobes, using a creaser element coupled to the lower lip shaper. Also a central platform may be coupled to either a lip shaper such that the upper and lower lips are at least partially separated during use of the lip enhancement and enlargement device.

Each type of lip enhancement and enlargement device may also include one or more additional components that relate to device assembly, and which alleviate potential side effects of applying negative pressure to lips. For example, after insertion of a lip shaper assembly into an opening defined in the suction element, a retainer element may be positioned around an outer face of the suction element to hold the lip shaper assembly securely in place. Each device may also include a mark prevention element positioned around at least one outer face of a lip shaper. The mark prevention element may be manufactured from a flexible material, such as silicone, which helps to prevent marks, bruises, and indentations during and after device use. A cover may also be included with each device for decorative and protection purposes. A blocker element is another optional component, which may be inserted into a cavity of the lip shaper assembly to alleviate negative pressure on a portion of the upper and lower lips.

Also disclosed herein is a lip enhancement and enlargement kit which can include a suction element, an upper lip shaper, and a first type of lower lip shaper disposed at least partially within a package. The kit may include a second type of lower lip shaper, a retainer element, a mark prevention element, a cosmetic and a cover at least partially disposed within the package.

Methods for lip enhancement and enlargement include inserting one or both lips of a user into a lip enhancement and enlargement device having a lip shaper coupled to a suction element; pressurizing the suction element to apply partial vacuum pressure to at least a portion of one or both lips and seal around a surrounding lip area; breaking the seal from the surrounding lip area; and removing the lip enhancement and enlargement device from the surrounding lip area. The suction element may be pressurized, using any known method, including manual pressurization.

A more complete understanding of the lip enhancement and enlargement devices, kits, and methods disclosed herein will be afforded to those skilled in the art, as well as a realization of additional advantages and objects thereof, by consideration of the following detailed description. Reference will be made to the appended sheets of drawings which will first be described briefly.

BRIEF DESCRIPTION OF THE DRAWINGS

The drawings described herein are for illustrative purposes and are not intended to limit the scope of the present disclosure. Like element numerals may be used to indicate like elements appearing in one or more of the figures.

FIG. 3A is an exploded perspective view of an embodiment of a lip enhancement and enlargement device.

FIG. 27A is a front view of a user before application of a lip enhancement and enlargement device.

FIG. 27B is a front view of a user after application of a lip enhancement and enlargement device.

FIG. 28A is a front view of a user before application of a lip enhancement and enlargement device.

FIG. 28B is a front view of a user after application of a lip enhancement and enlargement device.

DETAILED DESCRIPTION

Figure 1:
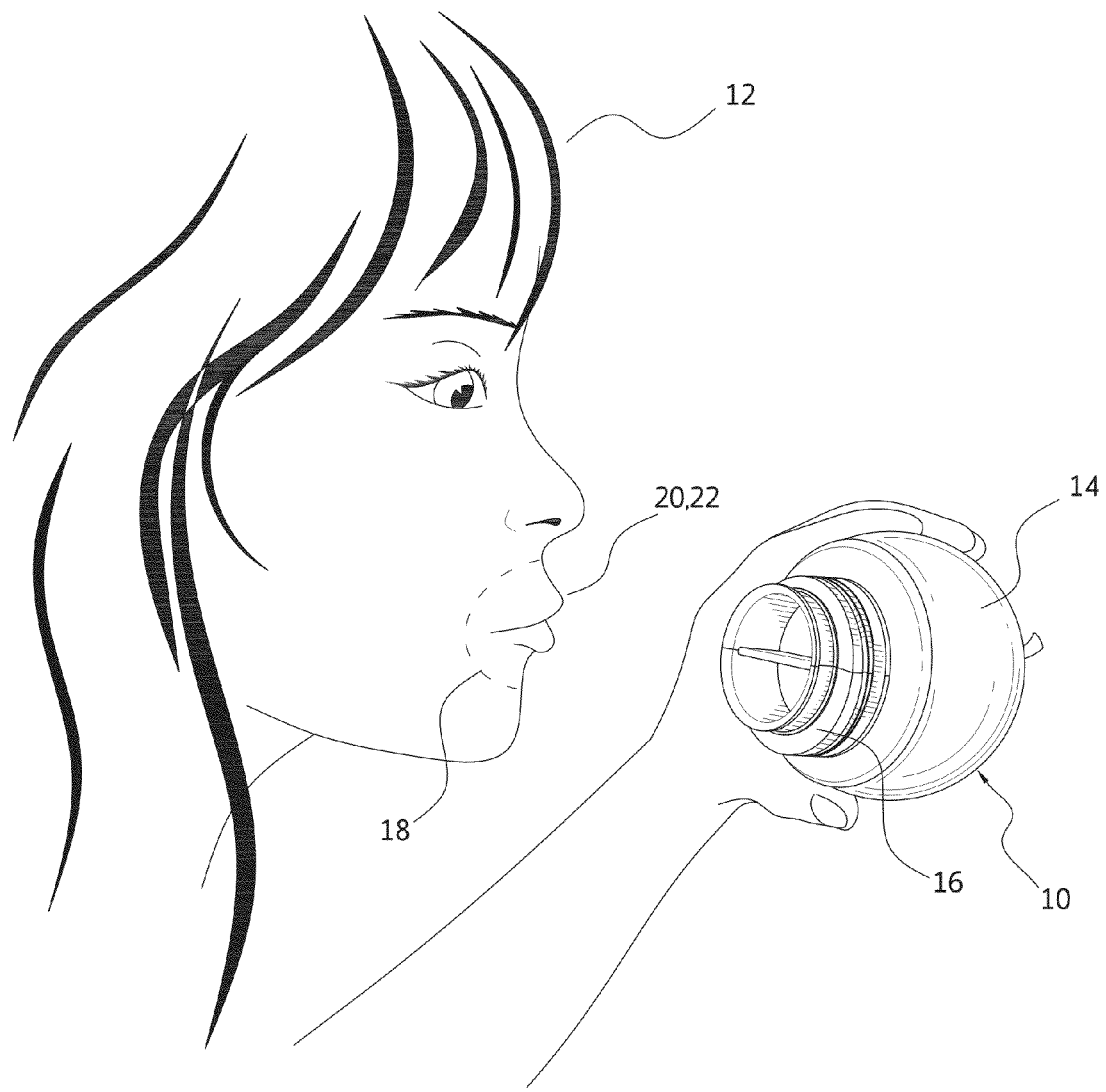
FIG. 1 is a perspective view of a lip enhancement and enlargement device, being held by a user.

Turning in detail to the drawings, FIG. 1 shows a lip enhancement and enlargement device 10 being held by a user 12. Each type of lip enhancement and enlargement device 10, 100 (FIGS. 5A-5C) includes a suction element 14 and a lip shaper 50, 52a, 52b (FIGS. 11A-11C) that may be included in a lip shaper assembly 16 coupled to the suction element. Although the lip shaper 60 is depicted as having a perimeter ring in a circular shape, it should be appreciated that other perimeter shapes may also be useful, for example, elliptical shapes. When a user 12 places his/her lips inside a lip shaper assembly and activates a suction element, the device enlarges and enhances the user's lip structure 22 by creating a seal around the surrounding lip area 18 and applying a partial vacuum to lip tissue 20 and lip structure 22 (FIG. 2B). Specifically, the suction element 14 is configured to apply suction forces to lip tissue 20 and lip structure 22 such that at least a portion of lip tissue and structure extends into at least one lip shaper. Because of these forces, blood circulation in the lip area increases, causing swelling and enlargement of lips.

Elements included within a lip shaper and/or a lip shaper assembly, however, are not limited to elements that cause lip enlargement. Lip shapers and lip shaper assemblies can include various elements, which correct misshaped lips and/or mismatched lips, alleviate the potential for lip misshaping associated with lip enlargement devices (e.g. lip pumps), and assist with the development of specific lip features. Depending on the configuration of a lip shaper 50, 52a, 52b (FIGS. 11A-11C), and lip shaper assembly 16, specific portions of lip structure 22 can be shaped, according to user preference. Although the lip shapers 50, 52a, 52b are depicted as generally circular at their outer perimeters, it should be appreciated that lip shapers with elliptical outer perimeters may also be useful. In addition, or in the alternative, the size of a lip shaper may be smaller or larger than depicted herein.

Figure 2A:
FIG. 2A shows an exemplary view of a face after application of a lip enhancement and enlargement device.
Figure 2B:
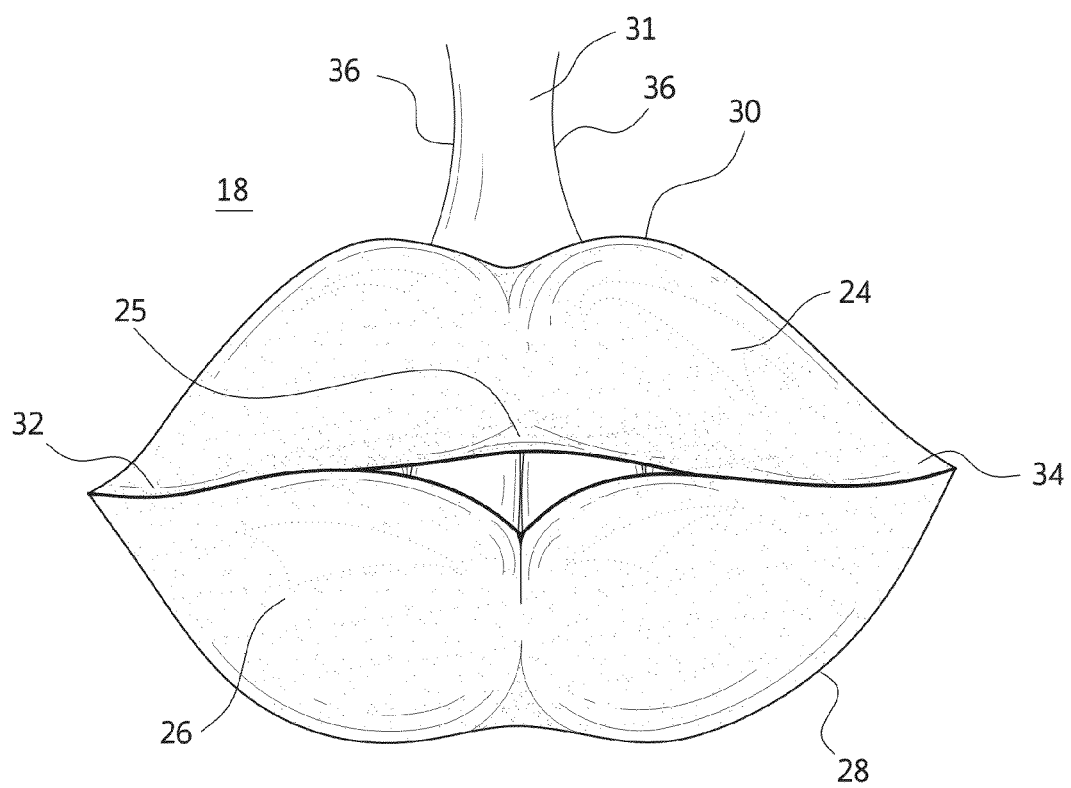
FIG. 2B shows an exemplary view of lip structure and lip tissue.

Referring to FIGS. 2A-2B, as used herein, lip structure 22 includes, but is not limited to: upper lip vermillion 24, upper lip tubercle 25, lower lip vermillion 26, vermillion border 28, Cupid's bow 30, philtrum 31, and left and right oral commissures 32, 34. The upper and lower lip vermillion 24, 26 refer to areas on the upper and lower lip areas, which are surrounded by the vermillion border 28. These areas, on some individual appear reddish or darker than the surrounding lip area 18. The Cupid's bow is the double curve of the upper lip, which is said to resemble the bow of Cupid, the Roman god of erotic love. The peaks of the bow substantially coincide with the philtral columns 36 giving a bowlike appearance to the lip. Through use of lip enhancement and enlargement devices 10, 100 one or more of these and other elements of lip structure 22 may be affected.

Figure 3B:
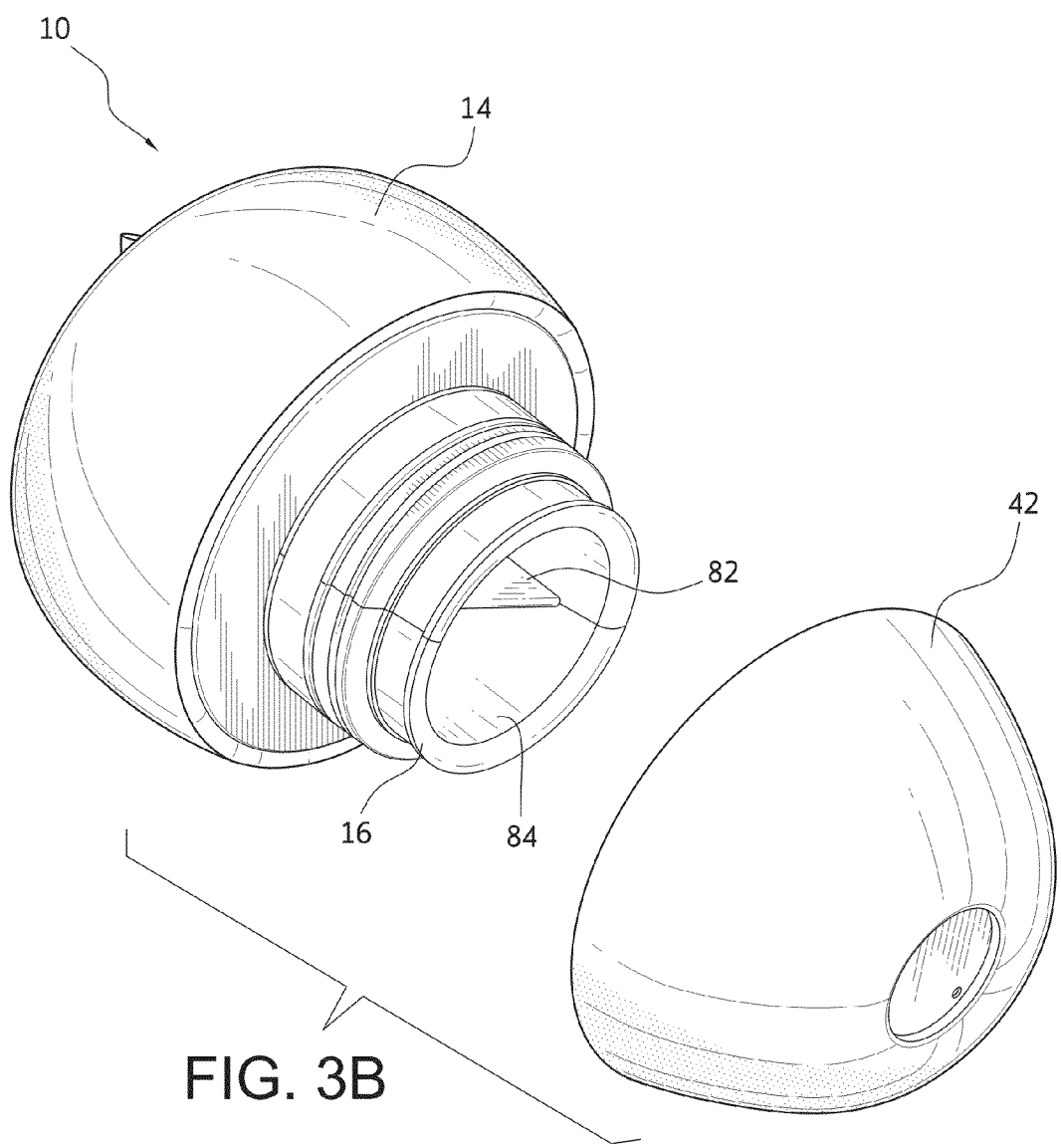
FIG. 3B is a partially exploded perspective view of the lip enhancement and enlargement device shown in FIG. 3A, excluding a mark prevention element.
Figure 3C:
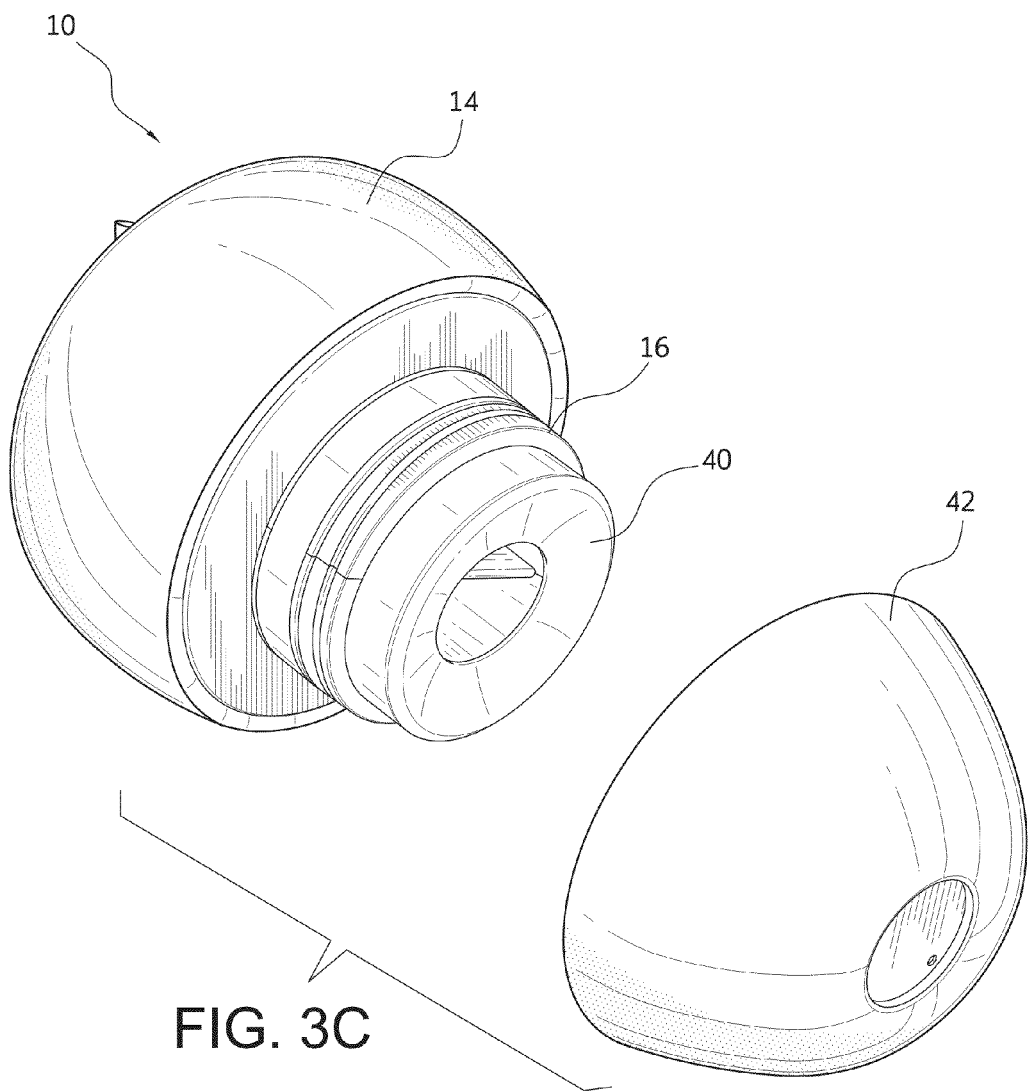
FIG. 3C is a partially exploded perspective view of the lip enhancement and enlargement device shown in FIG. 3A, including a mark prevention element.

FIG. 3A shows an exploded view of one configuration of a lip enhancement and enlargement device 10. In this configuration, the device includes a suction element 14, a lip shaper assembly 16, a retainer element 38, a mark prevention element 40, and a cover 42. The suction element 14 may be any device configured to apply partial negative pressure to lip tissue 20 and lip structure 22. As such, the suction element may be any type of pump or pumping device that can create a partial vacuum. In FIG. 3A, the suction element 14 includes one or more elastomeric materials, which cause the suction element to yield upon application of force to its outer surface 44. For this type of suction element, preferred materials include one or more elastomeric materials, e.g. various types of natural and synthetic rubbers and thermoplastic materials such as SANTOPRENE™ thermoplastic vulcanizate. An elastomeric suction element may be hand-pressurized; however, it may also be pressurized by any known method or device capable of creating a partial vacuum, e.g. methods and devices that initiate mechanical and/or electrical pressurization. Where the suction element is not manually or hand-driven, it may be coupled to a power source (not shown), for example, an electric power source that receives charges from an electric motor, battery, or solar element. Suction elements, as described herein, preferably have an opening 46 for coupling to a lip shaper assembly 16.

FIGS. 3A-5C show various views of lip enhancement and enlargement devices 10, 100. These configurations can include optional components, which can facilitate device assembly, alleviate potential side effects and/or lend to the aesthetic appearance of the lip enhancement and enlargement devices. Referring particularly to FIG. 3A, a lip enhancement and enlargement device can also include also a retainer element 38, a mark prevention element 40, and a cover 42. The lower and upper lip shapers 50, 52a are positioned against each other to form the lip shaper assembly 16. Upon assembly, the upper and lower lip shapers are inserted into opening 46 of the suction element 14. The retainer element 38 is configured to retain the lip shaper assembly 16 in the opening 46, by positioning the element around an outer face 39 of the suction element. The retainer element is preferably manufactured from a flexible material, e.g. an elastomeric material or spring metal such that a user may remove the retainer element 38, allowing for removal of the lip shaper assembly and replacement of the second type of lower lip shaper 52b for the first type of lower lip shaper 52a. In device configurations where replacement of alternative lip shapers is not an option, a retainer element may be excluded from the device. In these types of configurations, a lip shaper assembly 16 may be coupled to a suction element using mechanical fasteners, adhesives, or other methods or devices that allow the lip shaper assembly to be held within opening 46. Although the lip shaper assembly is shown have a substantially circular outer surface, alternative shapes for the assembly may be implemented. For examples, a lip shaper assembly may have an elliptical outer shape.

A lip enhancement and enlargement device may also include a mark prevention element 40, which is configured to prevent marks, grooves, and/or indentations that could be formed on the surrounding lip area 18 (FIG. 1), during application of the device. See also FIGS. 11A-11C (showing a lip enhancement and enlargement device in use). The mark prevention element 40 is configured for placement around outer faces 41 the lip shaper assembly 16, as particularly shown in FIGS. 3A, 3C, 4D, and 5C. The mark prevention element 40 also includes a concave area 54, defining an opening 56. The mark prevention element 40 is manufactured from one or more flexible materials such that a device 10, 100 leaves minimal or relatively little indentations, markings, grooves, and/or bruises on a user's skin after use of the device. Preferred materials comprise up to 100% of elastomeric materials, including various types of rubber-based and silicone-based products which are food and/or medical grade.

Figure 8:
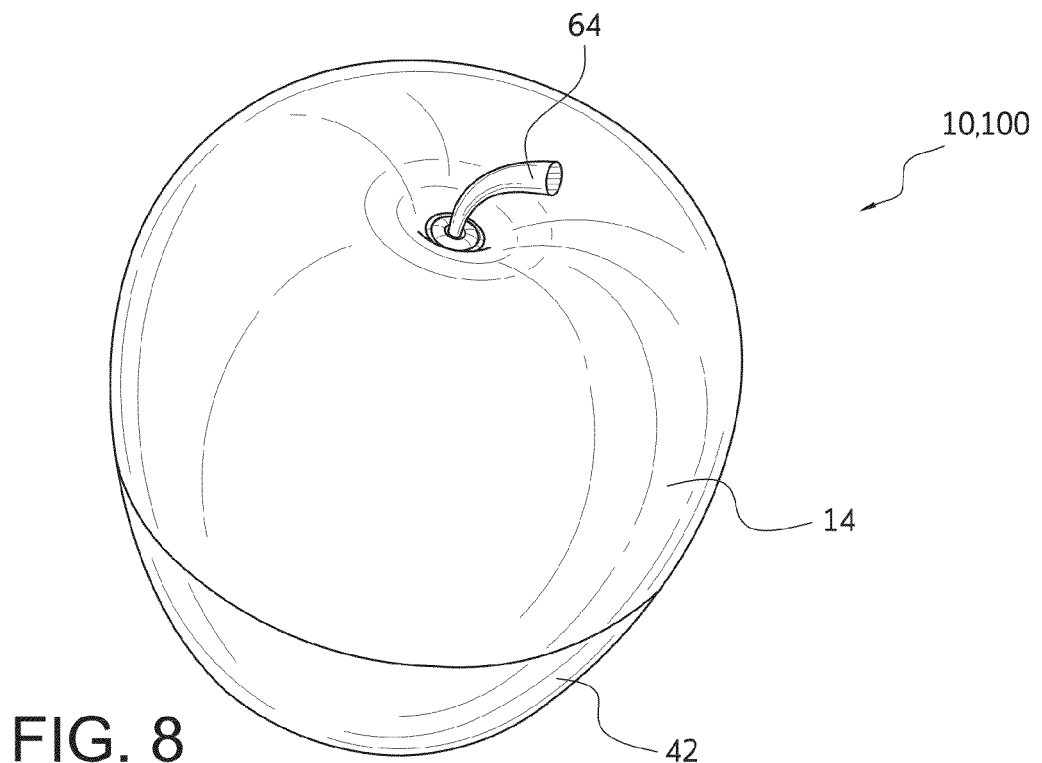
FIG. 8 is a front perspective view of one embodiment of a lip enhancement and enlargement device.
Figure 9:
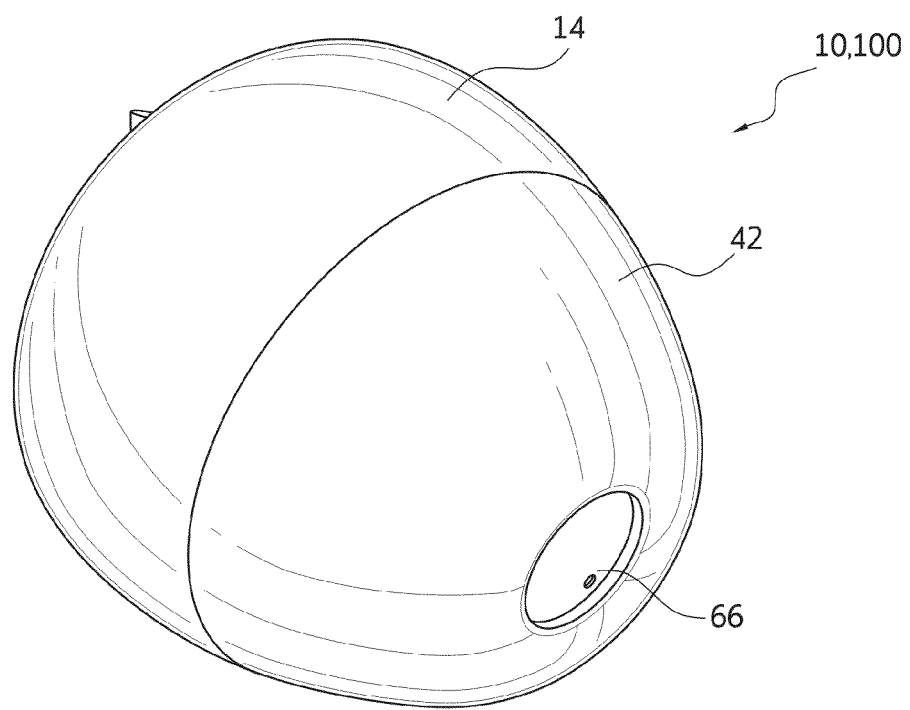
FIG. 9 is rear perspective view of the lip enhancement and enlargement device shown in FIG. 8.

The cover 42 is an optional component which can serve to protect the lip shaper assembly during storage and transport, for example. One or more fastening elements 58, such as threads or tangs, may also be disposed within the cover 42 such that the cover securely and removably engages with one or more mating elements 59, e.g. mating threads or notches, on the lip shaper assembly 16 (FIG. 3A). Preferably, the cover 42 has a size and shape that lends to the aesthetic appearance of a lip enhancement and enlargement device. FIGS. 8 and 9 show one device configuration in which a fully assembled device looks like an apple, with the cover 42 and suction element appearing to be halves of an apple. One or more decorative elements may also be included within the suction element and/or the cover for aesthetic purposes. FIG. 8, for example, shows a stem-shaped element 64 incorporated into a section of the suction element 14. The cover 42 also includes a recess 66 which lends to the aesthetic appearance of the device. Although the outer appearance of the lip enhancement and enlargement devices shown herein has an apple-like shape, the device can potentially have any shape. Preferably, the shape is such that the lip enhancement and enlargement device appears to be a decorative item suitable for placement on a bookshelf or desk. For example, the overall outer appearance of a lip enhancement and enlargement device may look similar to a piece of fruit, knickknack or other decorative element.

Figure 4A:
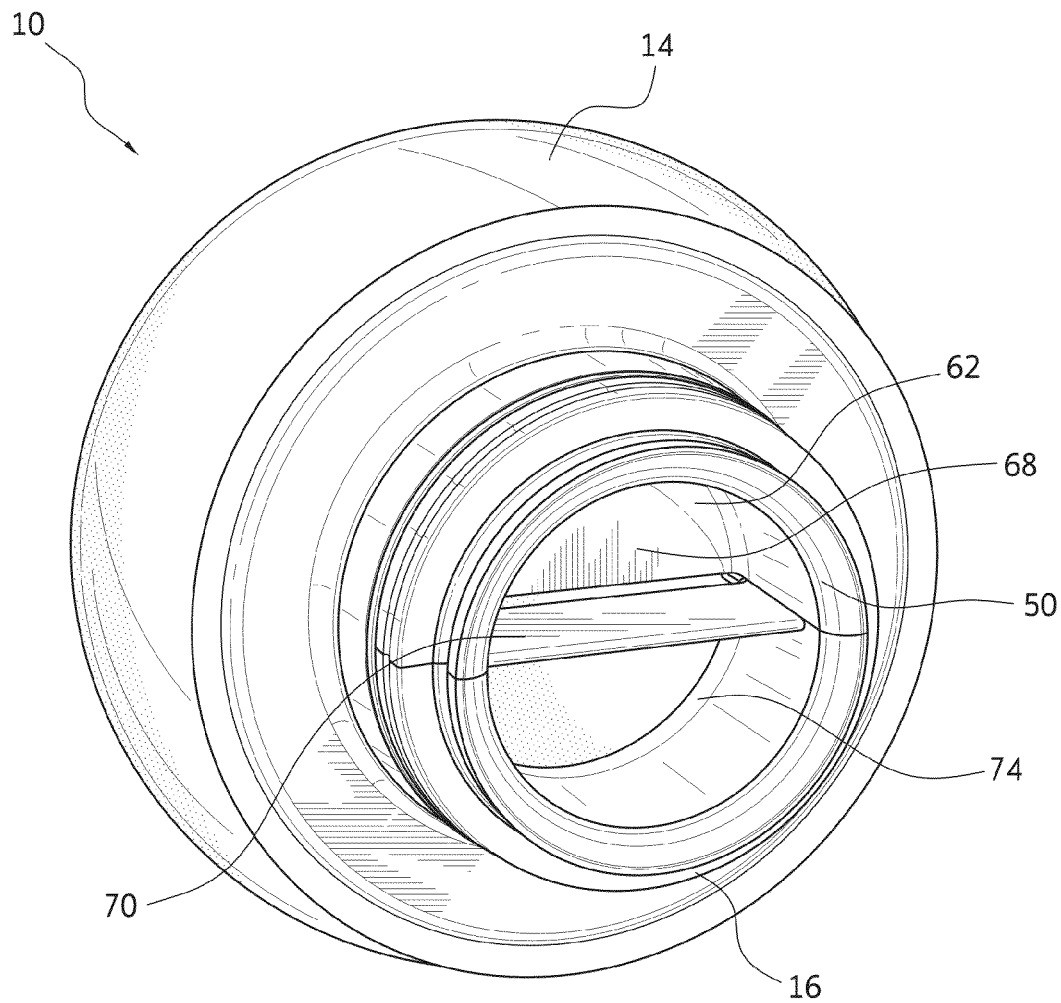
FIG. 4A is a perspective view of an embodiment of a lip enhancement and enlargement device.
Figure 4B:
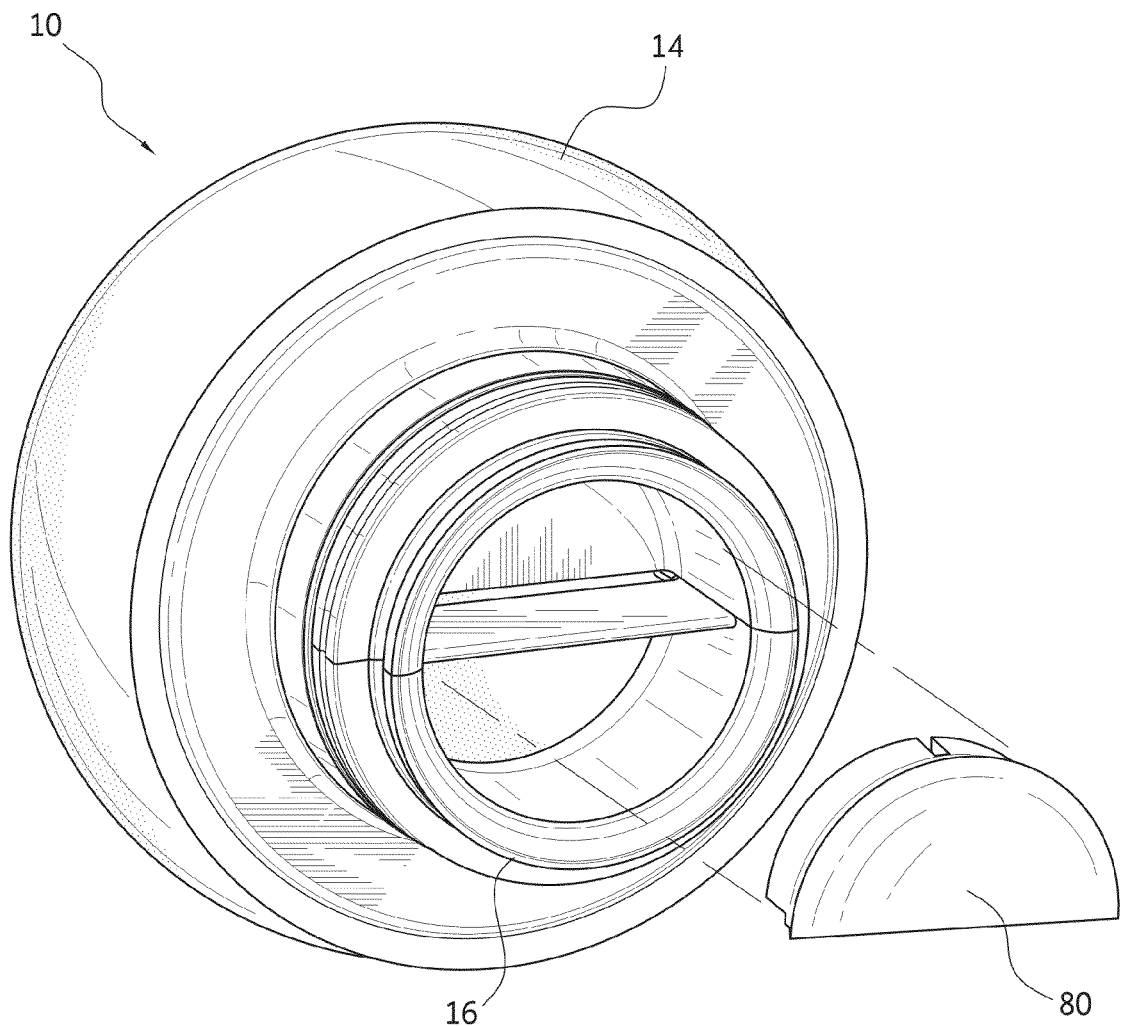
FIG. 4B is a perspective view of the lip enhancement and enlargement device shown in FIG. 4A, showing alignment of a blocking element with an upper cavity.
Figure 4C:
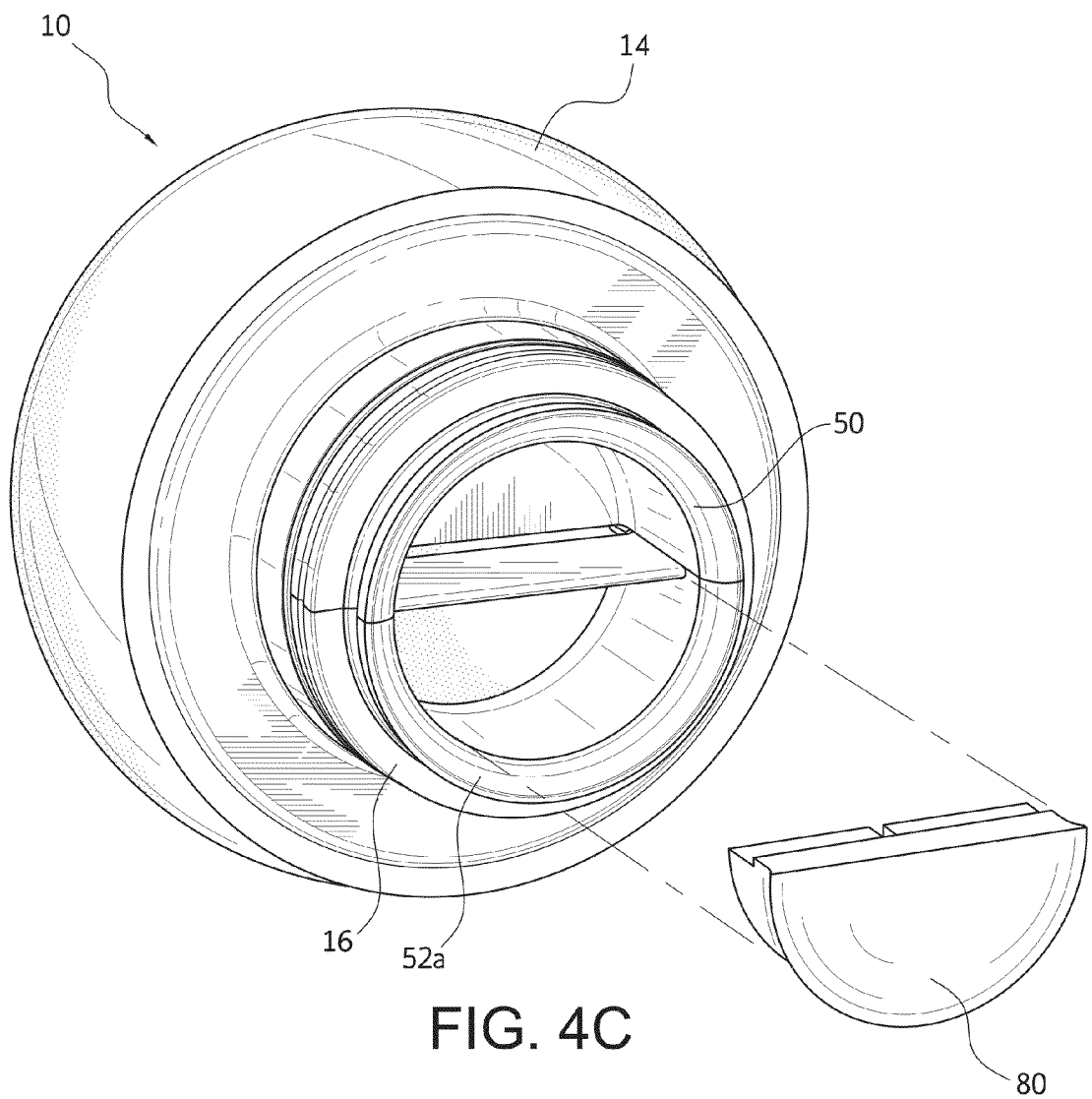
FIG. 4C is a perspective view of the lip enhancement and enlargement device shown in FIG. 4A, showing alignment of a blocking element with a lower cavity.
Figure 4D:
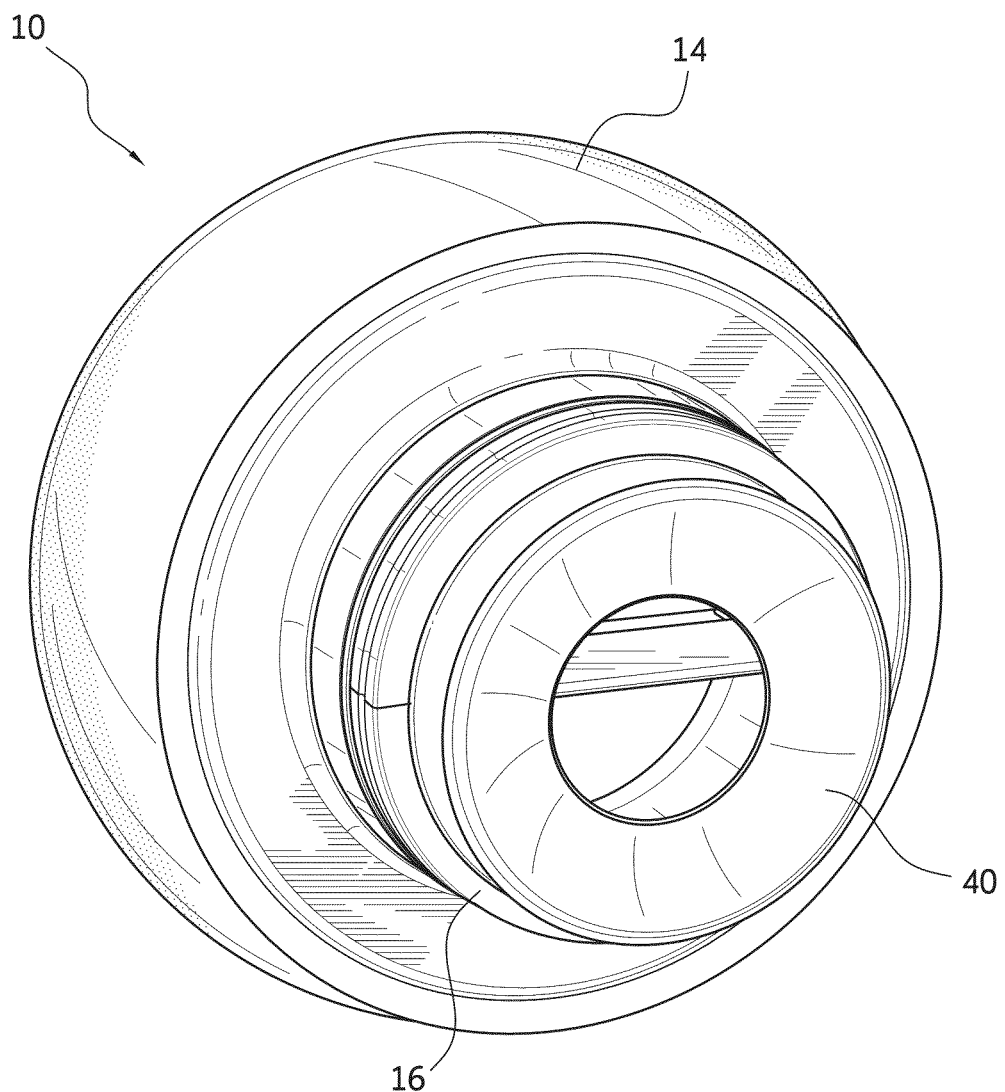
FIG. 4D is a perspective view of the lip enhancement and enlargement device shown in FIG. 4A with a mark prevention element.
Figure 6:
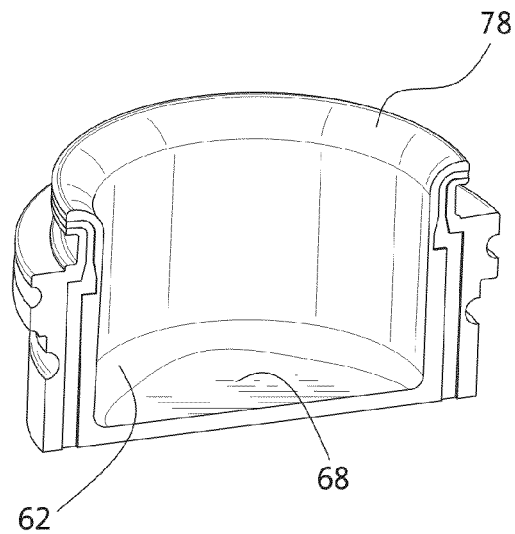
FIG. 6 is a perspective view of an upper lip shaper.

Each type of lip shaper includes features for enhancement and enlargement of lip tissue 20 and/or lip structure 22 (FIGS. 2A, 2B) and prevention of lip misshaping and development of marks, indentations, and/or bruising after use of a lip enhancement and enlargement device. Referring to FIGS. 4A, 4B, and 6, the upper lip shaper 50 includes a rear wall 68 that prevents excessive pulling of the upper lip, and particularly excessive pulling of the upper lip tubercle 25 (FIG. 2B). This type of pulling is known to cause a "ducky" upper lip. The rear wall 68 can be adjustable and/or deformable such that its positioning in the lip shaper 50 may be changed. The upper lip shaper 50 also includes at least one radiused contouring element 62, which acts to shape upper lip structure, including the Cupid's bow and the philtrum. The contouring element 62 can extend fully or partially around an edge of the upper lip shaper 50 such that during use of the device upper lip structure is shaped by the contouring element 62. The contouring element may be configured, for example, to lift the upper lip and shorten the philtrum 31 (FIG. 2B). The contouring element 62 may be configured as more clearly shown in FIG. 6.

The lip shaper assembly 16 also includes a lower lip shaper (52a or 52b) for shaping and contouring of the lower lip. Coupled to either type of lower lip shaper and positioned between the upper and lower lip shapers upon assembly is a central platform 70. The central platform is used to separate the upper and lower lips during use of the lip enhancement and enlargement device. The central platform 70 also contours an underside portion of the lower lip which is pressed against the platform such that grooves and/or pits in the lower lip are less visible after use of a lip enhancement and enlargement device. The central platform 70 may also be provided with a slotted area 72 which reduces the suction in the upper cavity 82. This will further prevent the development of a "ducky" upper lip.

Figure 7A:
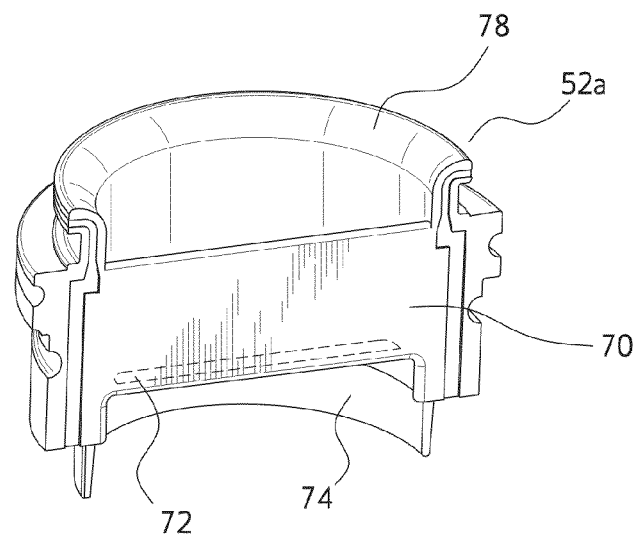
FIG. 7A is a perspective view of a first type of a lower lip shaper.
Figure 7B:
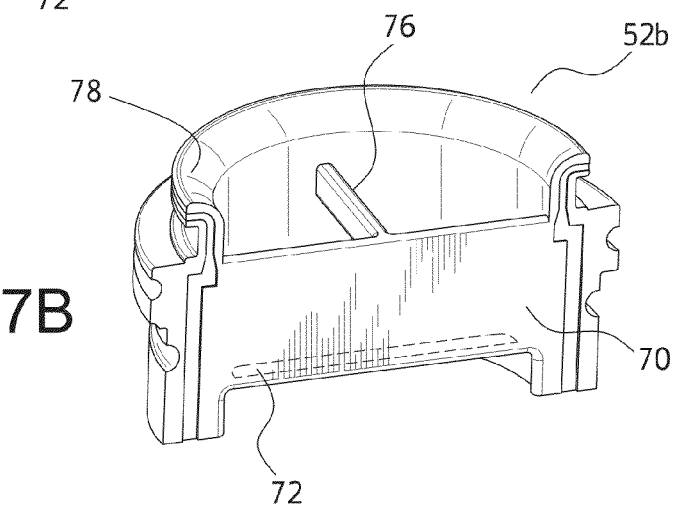
FIG. 7B is a perspective view of a second type of a lower lip shaper.

FIGS. 7A and 7B show two types of lower lip shapers 52a, 52b, which may be included in a lip shaper assembly. A first type of lower lip shaper 52a may be used for development of a fuller unitary lower lip lobe after use of the lip enhancement and enlargement device. This type of lower lip shaper may also include an extension 74, which prevents pulling of the lower lip into the suction element. A second type of lip shaper 52b includes a creaser element 76 for development of a crease on the lower lip such that the lower lip appears to have two fuller lip lobes after use of the device 100. The creaser element 76 is preferably an elongated element that couples to the underside of the central platform 70. The creaser element 76 may also be adjustable and/or deformable such that the positioning of the crease may be positioned according to user preference. For example, the creaser element can be moved forward, backward, tilted forward or backward.

Each type of lip shaper includes one or more radiused edges 78, which also help to alleviate marks, indentations, and/or bruising, which may occur during use of a lip enhancement and enlargement device. These edges may also be formed to substantially fit a mark prevention element 40.

When assembled the upper lip shaper 50, the lower lip shaper (52a or 52b), and the central platform 70 form the lip shaper assembly 16 such that one or more cavities 82, 84 are may be used for placement of a user's lips. However, in certain situations a user may only want to enhance either the upper or the lower lip. For example, a male user, having a moustache would not necessarily have a need to use a lip enhancement and enlargement device to shape and contour upper lip structure. In this type of situation, a blocker element 80 may be inserted into either the upper cavity 82 or lower cavity 84, as shown in FIGS. 4B, 4C, 5B, and 5C. The blocker element 80 is shaped to fit the upper and lower cavities. Where the lip enhancement and enlargement device include the lower lip shaper 52b, the blocker element is provided with a groove or channel 81 (FIG. 5C) for positioning around the creaser element 76. Preferably, the blocker element is interchangeable (i.e. its positioning may be reversed) and made from a flexible elastomeric materials. Preferred materials include those having a durometer ranging from 40 to 70, Shore A.

Figure 10:
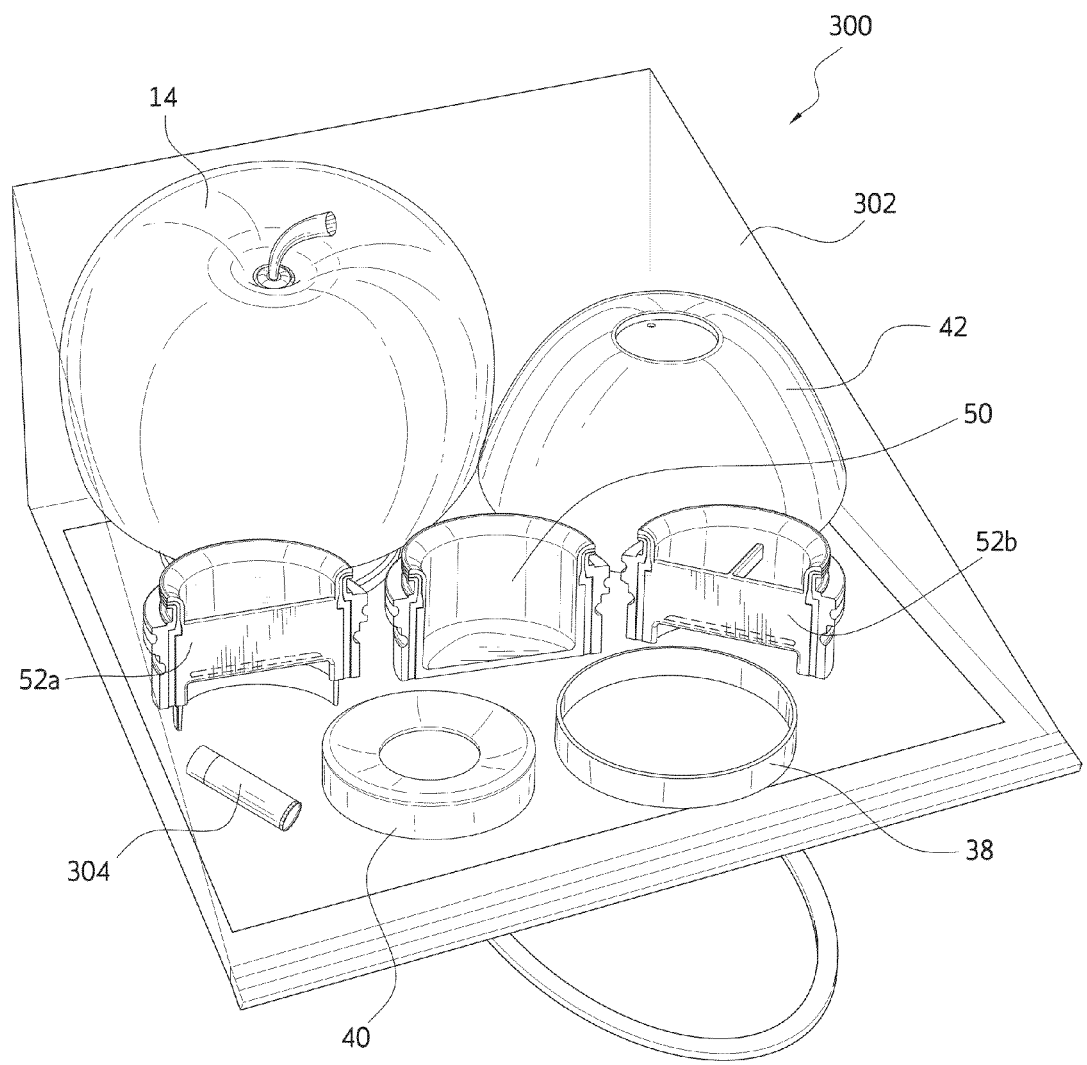
FIG. 10 is a top perspective view of a lip enhancement and enlargement kit.

FIG. 10 shows one configuration of a kit 300 for lip enhancement and enlargement, which includes a package 302, a suction element 14, an upper lip shaper 50, a first type of lower lip shaper 52a, a second type of lower lip shaper 52b, a retainer element 38, a mark prevention element 40, and a cover 42. Each of these elements is enclosed by the package 302. The kit 300 may also include one or more cosmetics 304, such as lip balms, lip plumpers, lip stain, lipstick, gel-based cosmetics and/or lip gloss, which may be applied after using the device. Although shown disassembled for illustrative clarity, it should be appreciated that the kit 300 may include at least some parts in an assembled configuration. Likewise, some parts may be omitted, and omitted parts provided as separate components or in supplemental kits, without departing from the scope of the present disclosure.

All features and components included in the lip shapers and lip shaper assemblies disclosed herein may be adjusted and/or deformed such that a user may manipulate the device to yield a desired lip shape. For example, one or more contouring elements may be included in a lower lip shaper and/or a creaser element may be included in an upper lip shapers. A lip enhancement and enlargement device may also include an upper or lower lip shaper alone. This latter configuration would be particularly useful for persons having moustaches that would not want negative pressure apply to an upper lip. As such, the configurations shown in FIGS. 1-10 or elsewhere herein should not be construed as limiting practice of the innovative concepts herein to the illustrated and described embodiments. The illustrated embodiments are merely representative configurations, which may be altered by one of ordinary skill without departing from the innovative concepts of the present disclosure.

Figure 11A:
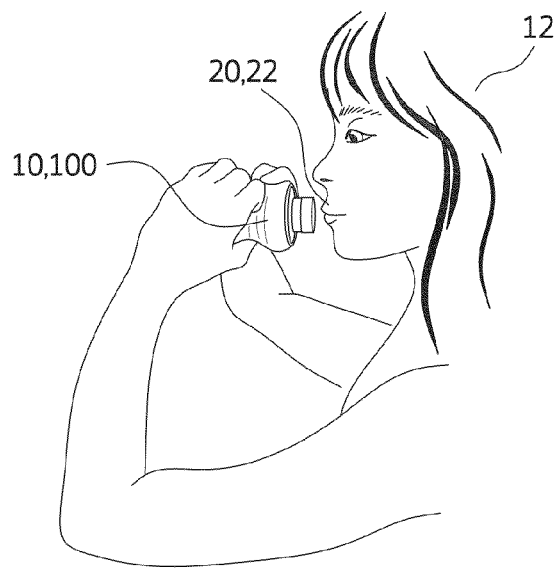
FIGS. 11A-11C are perspective views of a user, applying a lip enhancement and enlargement method, using a lip enhancement and enlargement device.
Figure 11B:
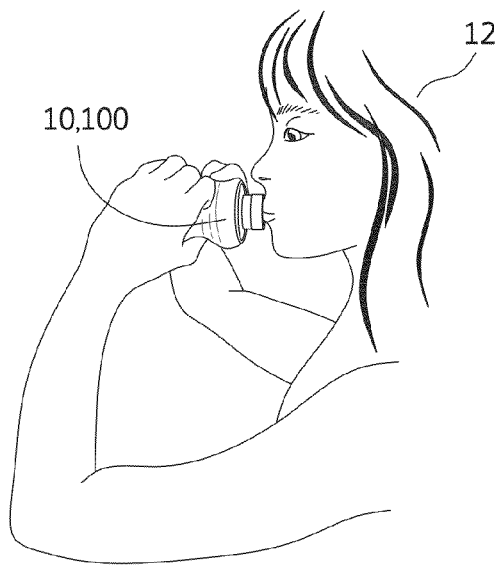
Figure 11C:
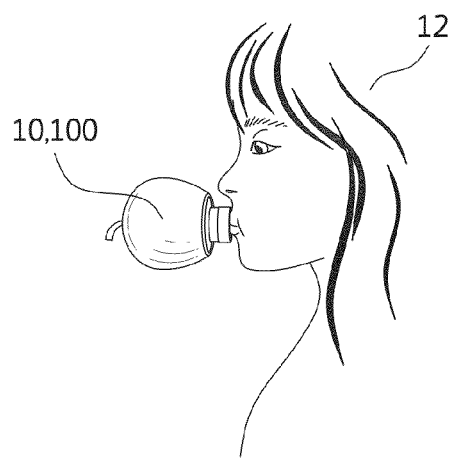
Figure 12:
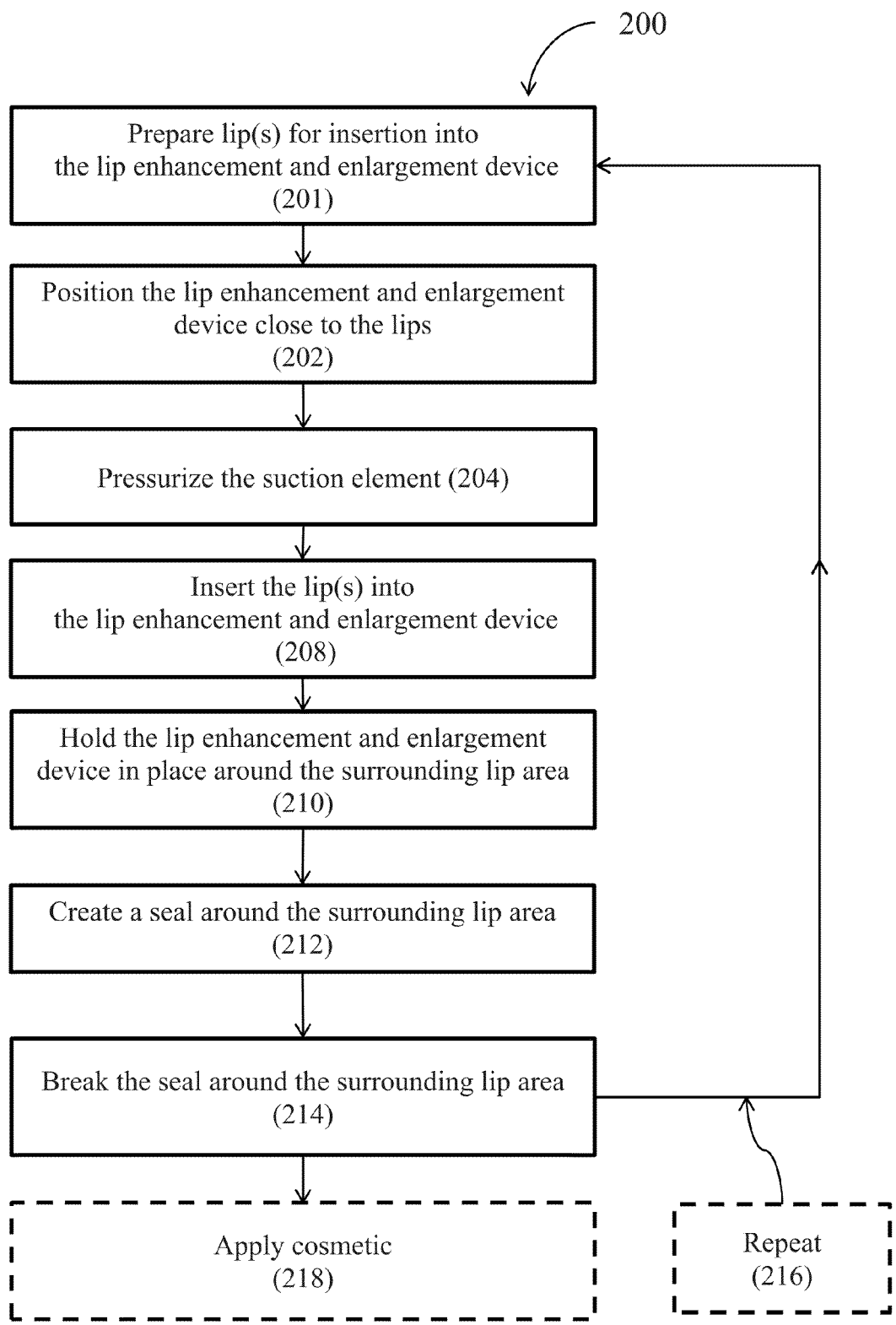
FIG. 12 is a flowchart, showing steps of a lip enhancement and enlargement method.

FIGS. 11A-11C illustrate selected operations in a method for lip enhancement and enlargement, which may include the method 200 illustrated in FIG. 12. Such methods may include various steps, which depend, in part, upon the type and extent of lip shaping and contouring desired by a user. Referring to FIGS. 11A-11C and 12, an initial step may include preparing a user's lips 201 for entry into the device 10, 100. The user may pucker the lips and press the lips together to facilitation insertion of the lips into the device. A suction element of the lip plumping device 10, 100 may be positioned about 1-inch to about 2-inches away from the user's lips 202 and then activated (FIG. 11B) 204 to prepare the device for applying a partial vacuum to lip tissue 20 and lip structure 22. Where the suction element comprises a resilient bladder manufactured from one or more elastomeric materials, for example, activation may be initiated by applying force to an outer surface of the suction element 206 to drive air out of a resilient bladder. The user may perform one or more operations for applying a lip enhancement and enlargement device having a lip shaper assembly coupled to a suction element to a face. The user may insert his or her into the device 208 and then hold the device in place for approximately two to four minutes 210. Enough of a partial vacuum should be created within the device such that a substantial seal is created 212 around the surrounding lip area 18, allowing the device to be held onto lip structure 22 without user assistance (FIG. 11C). Afterwards, the user may break the seal 214, by placement of a finger or other element at a rim of the device or slowing and gentle moving the device away from the lip structure. These steps may then be repeated for additional lip enhancement, enlargement, shaping, and contouring 216. Optionally, after use a cosmetic, e.g. a lip balm, gloss, or chemical-based lip plumper may be applied 218.

The foregoing method 200 may, in an alternative, be described as a lip enhancement and enlargement method, including an operation of applying a lip enhancement and enlargement device having a lip shaper assembly coupled to a suction element to a face. The method may further include creating a seal between the lip shaper and the face around a surrounding lip area, wherein the lip shaper assembly is configured to enable selective blocking of suction to any selected one of an upper lip or a lower lip. The method may further include applying suction to a selected one of the upper lip, lower lip, or both lips using the suction element and maintaining the vacuum for a period of time.

The innovative devices, including the lip shaper and blocker components, described herein may be used to select one of the upper lip, lower lip, or both lips for plumping. For example, a user may remove the blocker (80, FIG. 5B) from the lip shaper (16, FIG. 5B) to select both lips for plumping. In an alternative, the blocker 80 may be positioned in the upper part of the shaper 16 to select the lower lip only for plumping, or in the lower part of the shaper 16 to select the upper lip only for plumping (See, e.g., FIG. 5C). Thus, the method may include placing a suction blocking piece into one of an upper portion or lower portion of the lip shaper.

Similarly, a user may control whether or not to apply a lip creasing element by selecting one of a creaseless type of lower lip shaper 52a or a creasing type of lower lip shaper 52b as shown in FIG. 10 and elsewhere in the specification. Thus, the method may include contouring the selected one of the upper lip, lower lip, or both lips using a creaser element or creasing member coupled to the lip shaper. An example of a creasing member is pointed out in FIG. 5A at 76.

The lip enhancement and enlargement method may further include breaking the seal from the surrounding lip area after the period of time is elapsed as previously described. The method may further include removing the lip enhancement and enlargement device from the surrounding lip area, inspecting the lips and reapplying the foregoing steps if further enlargement is desired and no bruising or other tissue damage is observed from the application of suction.

As shown and described herein, applying suction may include compressing a resilient bladder to evacuate air, and then releasing compression of the bladder. This method may enable users to receive a tactile feel to the degree of suction being applied, as well as enable an aesthetically pleasing configuration of the bladder and lip enhancement and enlargement device. In other embodiments, other methods for applying suction may be used, for example using a small electric pump to evacuate air from a suction chamber, using a manually operated sliding piston and cylinder, or other method.

Examples

The following examples show users before and after use of the lip enhancement and enlargement devices disclosed herein. In these cases, results have been shown to last approximately one and one-half hours to two hours.

Figure 13A:
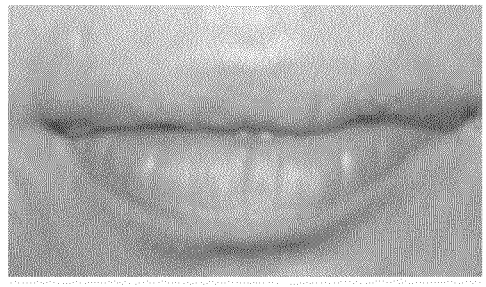
FIG. 13A is a front view of a user before application of a lip enhancement and enlargement device.
Figure 13B:
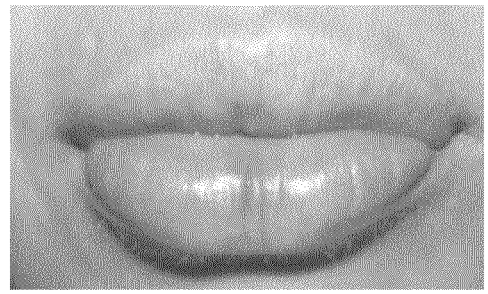
FIG. 13B is a front view of a user after application of a lip enhancement and enlargement device.

FIGS. 13A and 13B, respectively, show before and after front view of the lips of a Female, Age: 29, who applied a lip enhancement and enlargement device 10 shown in FIG. 4A for approximately two minutes. Afterwards, a lip enhancement and enlargement device 100 shown in FIG. 5A was applied for approximately two minutes.

Figure 5A:
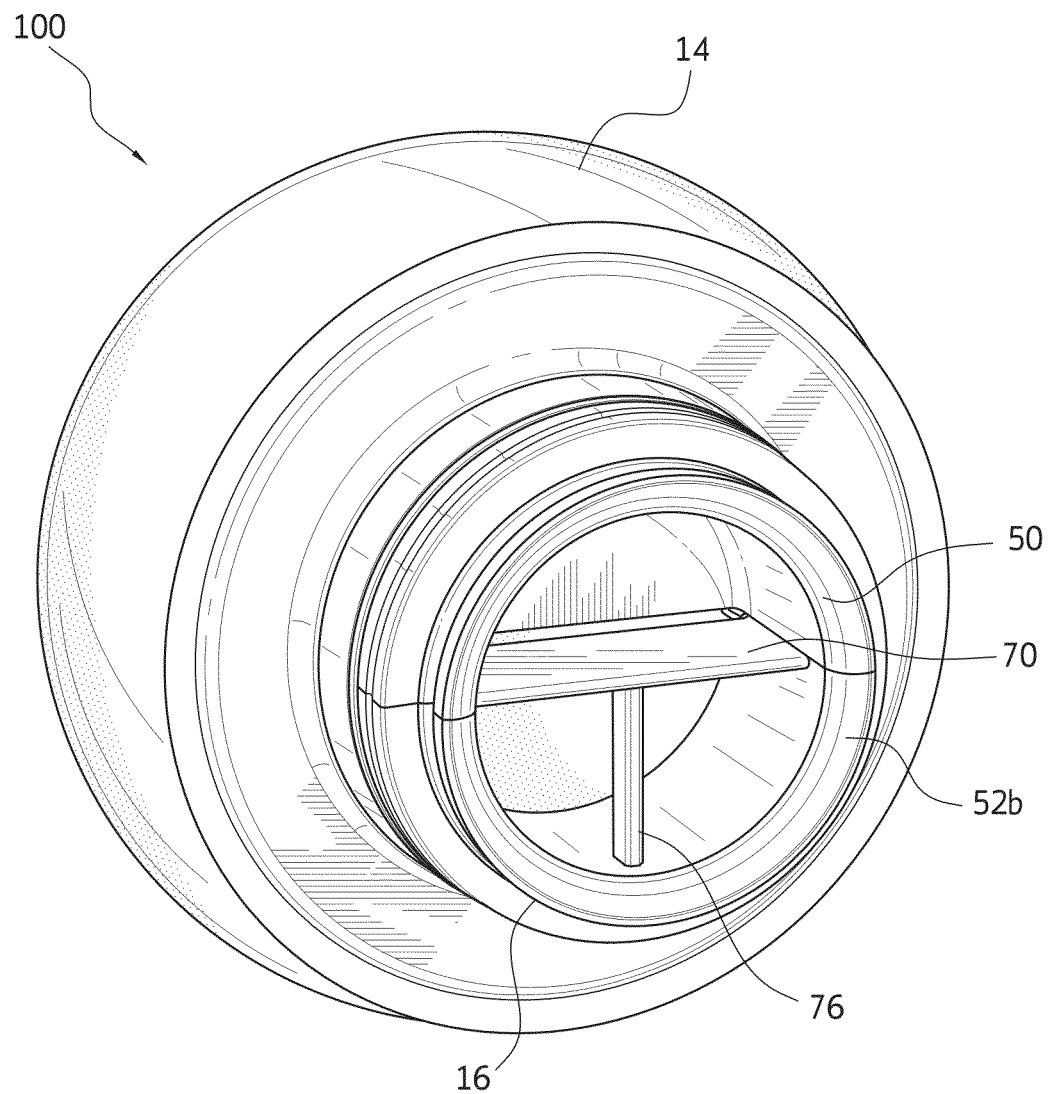
FIG. 5A is a perspective view a second embodiment of a lip enhancement and enlargement device.
Figure 14A:
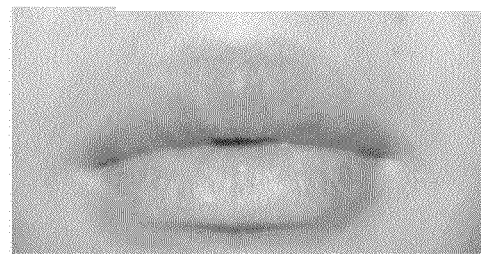
FIG. 14A is a front view of a user before application of a lip enhancement and enlargement device.
Figure 14B:
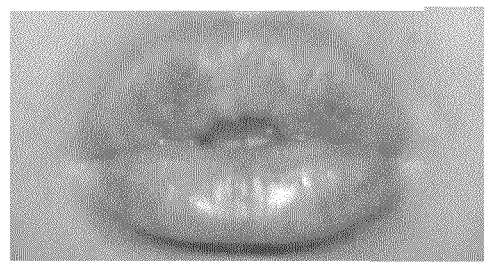
FIG. 14B is a front view of a user after application of a lip enhancement and enlargement device.

FIGS. 14A and 14B respectively, show before and after front views of the lips of a Female, Age: 15, who applied a lip enhancement and enlargement device 100 shown in FIG. 5A for approximately two minutes.

Figure 15A:
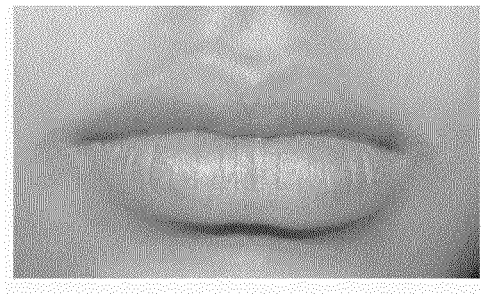
FIG. 15A is a front view of a user before application of a lip enhancement and enlargement device.
Figure 15B:
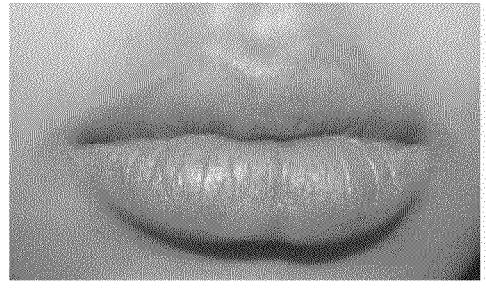
FIG. 15B is a front view of a user after application of a lip enhancement and enlargement device.

FIGS. 15A and 15B respectively, show before and after front views of the lips of a Female, Age: 15, who applied a lip enhancement and enlargement device 100 shown in FIG. 5A for approximately two minutes.

Figure 16A:
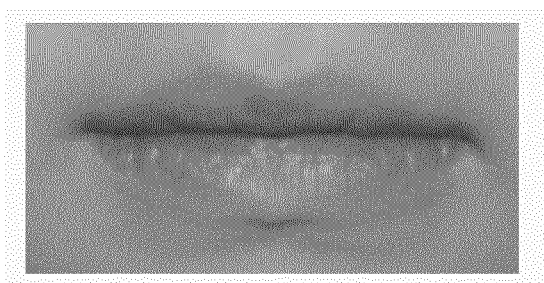
FIG. 16A is a front view of a user before application of a lip enhancement and enlargement device.
Figure 16B:
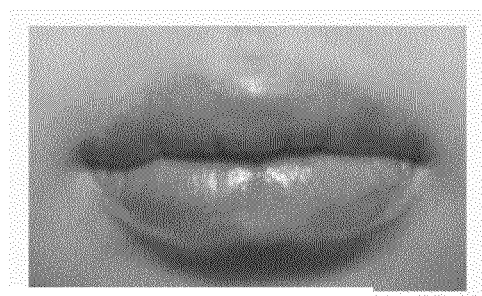
FIG. 16B is a front view of a user after application of a lip enhancement and enlargement device.

FIGS. 16A and 16B respectively, show before and after front views of the lips of a Female, Age: 17, who applied a lip enhancement and enlargement device 100 shown in FIG. 5A for approximately three minutes.

Figure 17A:
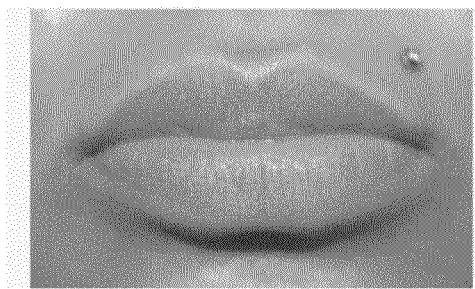
FIG. 17A is a front view of a user before application of a lip enhancement and enlargement device.
Figure 17B:
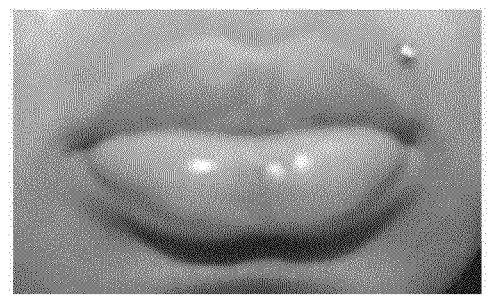
FIG. 17B is a front view of a user after application of a lip enhancement and enlargement device.

FIGS. 17A and 17B respectively, show before and after front views of the lips of a Female, Age: 19, who applied a lip enhancement and enlargement device 100 shown in FIG. 5A for approximately two minutes.

Figure 18A:
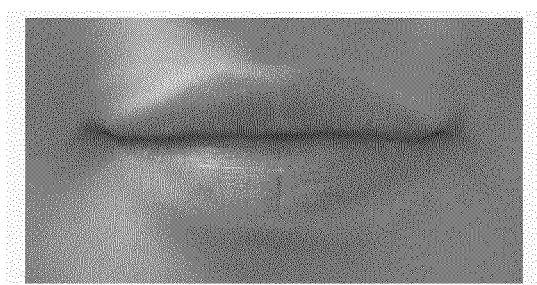
FIG. 18A is a front view of a user before application of a lip enhancement and enlargement device.
Figure 18B:
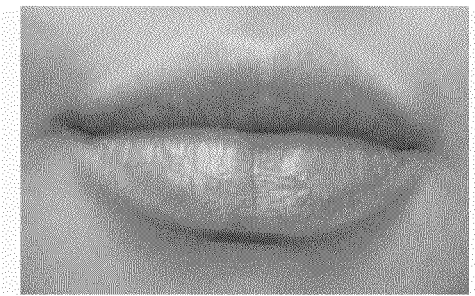
FIG. 18B is a front view of a user after application of a lip enhancement and enlargement device.

FIGS. 18A and 18B respectively, show before and after front views of the lips of a Female, Age: 20, who applied a lip enhancement and enlargement device 100 shown in FIG. 5A for approximately two minutes.

Figure 19A:
FIG. 19A is a front view of a user before application of a lip enhancement and enlargement device.
Figure 19B:
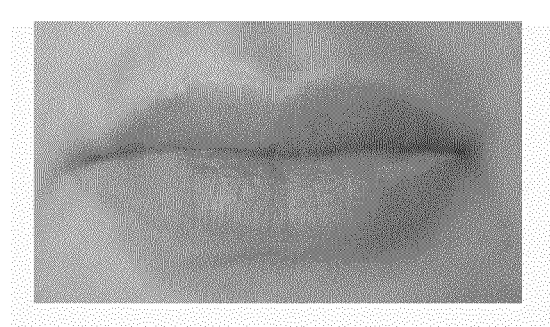
FIG. 19B is a front view of a user after application of a lip enhancement and enlargement device.

FIGS. 19A and 19B respectively, show before and after front views of the lips of a Female, Age: 29, who applied a lip enhancement and enlargement device 10 shown in FIG. 4A for approximately two minutes.

Figure 20A:
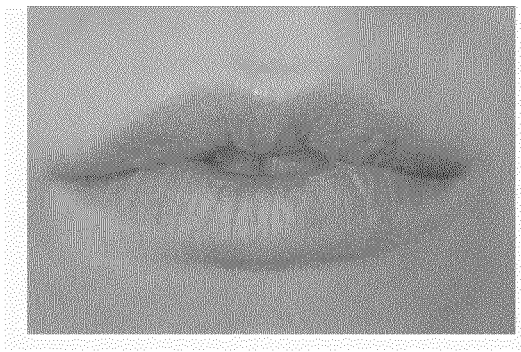
FIG. 20A is a front view of a user before application of a lip enhancement and enlargement device.
Figure 20B:
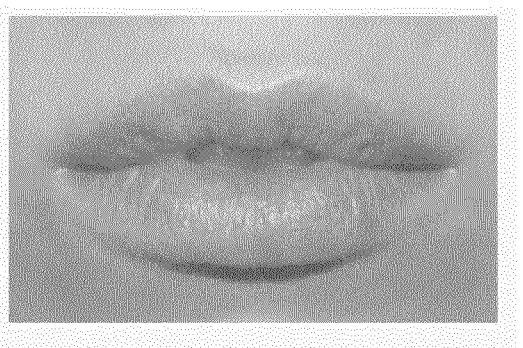
FIG. 20B is a front view of a user after application of a lip enhancement and enlargement device.

FIGS. 20A and 20B respectively, show before and after front views of the lips of a Female, Age: 20, who applied a lip enhancement and enlargement device 10 shown in FIG. 4A for approximately two minutes.

Figure 21A:
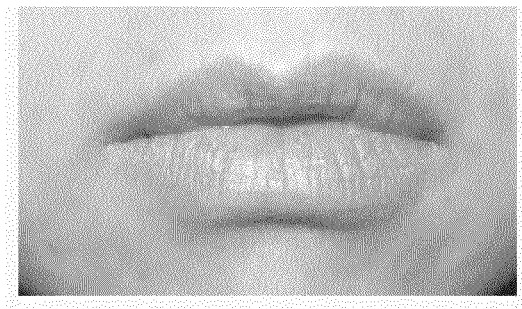
FIG. 21A is a front view of a user before application of a lip enhancement and enlargement device.
Figure 21B:
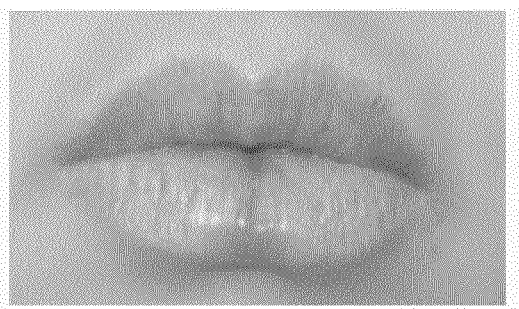
FIG. 21B is a front view of a user after application of a lip enhancement and enlargement device.

FIGS. 21A and 21B respectively, show before and after front views of the lips of a Female, Age: 42, who applied a lip enhancement and enlargement device 100 shown in FIG. 5A for approximately two minutes.

Figure 22A:
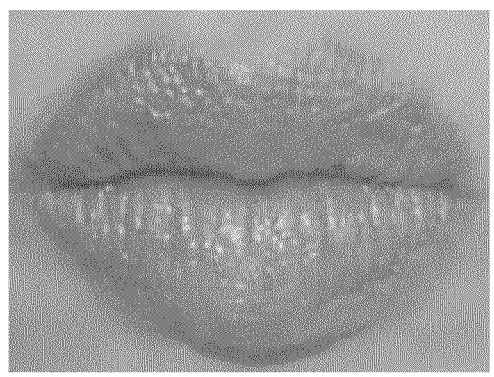
FIG. 22A is a front view of a user before application of a lip enhancement and enlargement device.
Figure 22B:
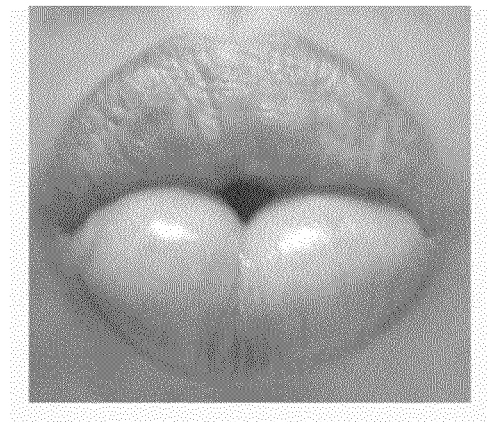
FIG. 22B is a front view of a user after application of a lip enhancement and enlargement device.

FIGS. 22A and 22B respectively, show before and after front views of the lips of a Female, Age: 44, who applied a lip enhancement and enlargement device 10 shown in FIG. 4A for approximately two minutes. Afterwards, a lip enhancement and enlargement device 100 shown in FIG. 5A was applied for approximately four minutes.

Figure 23A:
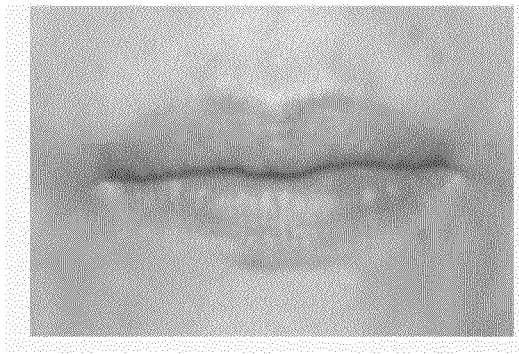
FIG. 23A is a front view of a user before application of a lip enhancement and enlargement device.
Figure 23B:
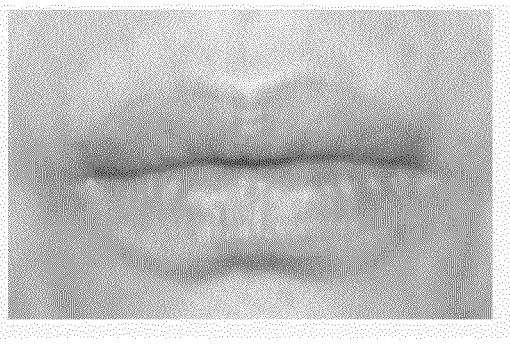
FIG. 23B is a front view of a user after application of a lip enhancement and enlargement device.

FIGS. 23A and 23B respectively, show before and after front views of the lips of a Male, Age: 55, who applied a lip enhancement and enlargement device 10 shown in FIG. 4A for approximately two minutes.

Figure 24A:
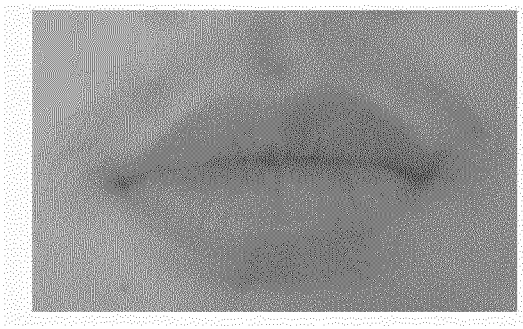
FIG. 24A is a front view of a user before application of a lip enhancement and enlargement device.
Figure 24B:
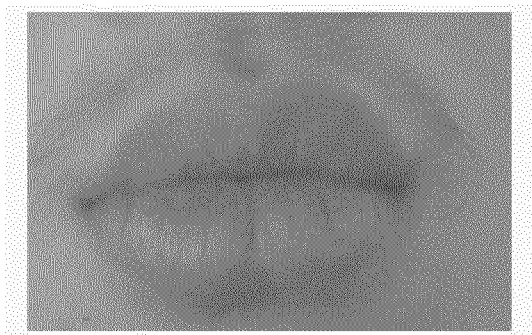
FIG. 24B is a front view of a user after application of a lip enhancement and enlargement device.

FIGS. 24A and 24B respectively, show before and after front views of the lips of a Male, Age: 18, who applied a lip enhancement and enlargement device 100 shown in FIG. 5A for approximately two minutes.

Figure 25A:
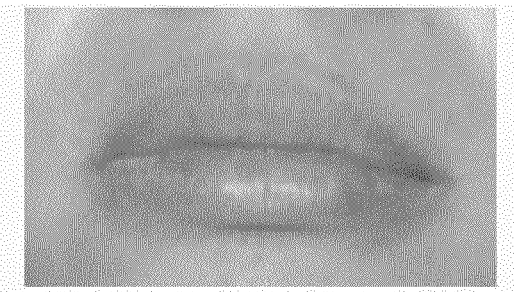
FIG. 25A is a front view of a user before application of a lip enhancement and enlargement device.
Figure 25B:
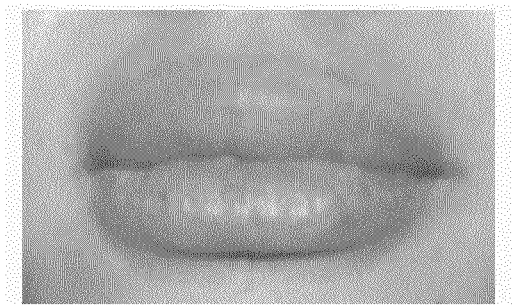
FIG. 25B is a front view of a user after application of a lip enhancement and enlargement device.

FIGS. 25A and 25B respectively, show before and after front views of the lips of a Male, Age: 28, who applied a lip enhancement and enlargement device 10 shown in FIG. 4A for approximately two minutes.

Figure 26A:
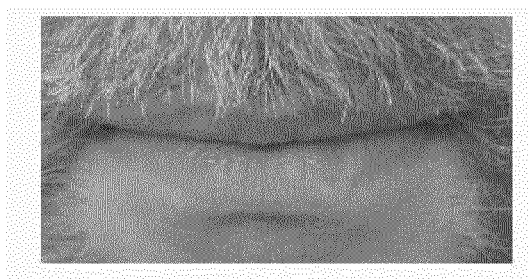
FIG. 26A is a front view of a user before application of a lip enhancement and enlargement device.
Figure 26B:
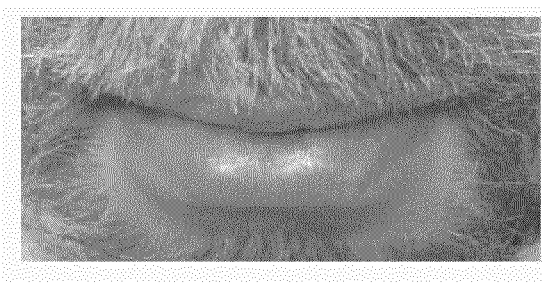
FIG. 26B is a front view of a user after application of a lip enhancement and enlargement device.

FIGS. 26A and 26B respectively, show before and after front views of the lips of a Male, Age: 44, who applied a lip enhancement and enlargement device 10 shown in FIG. 4B for approximately two minutes, where a blocker element was inserted into the upper lip shaper cavity.

FIGS. 27A and 27B respectively, show before and after front views of the lips of a Male, Age: 45, who applied a lip enhancement and enlargement device 100 shown in FIG. 5A for approximately two minutes.

FIGS. 28A and 28B respectively, show before and after front views of the lips of a Male, Age: 70, who applied a lip enhancement and enlargement device 100 shown in FIG. 5A for approximately three minutes.

Figure 5B:
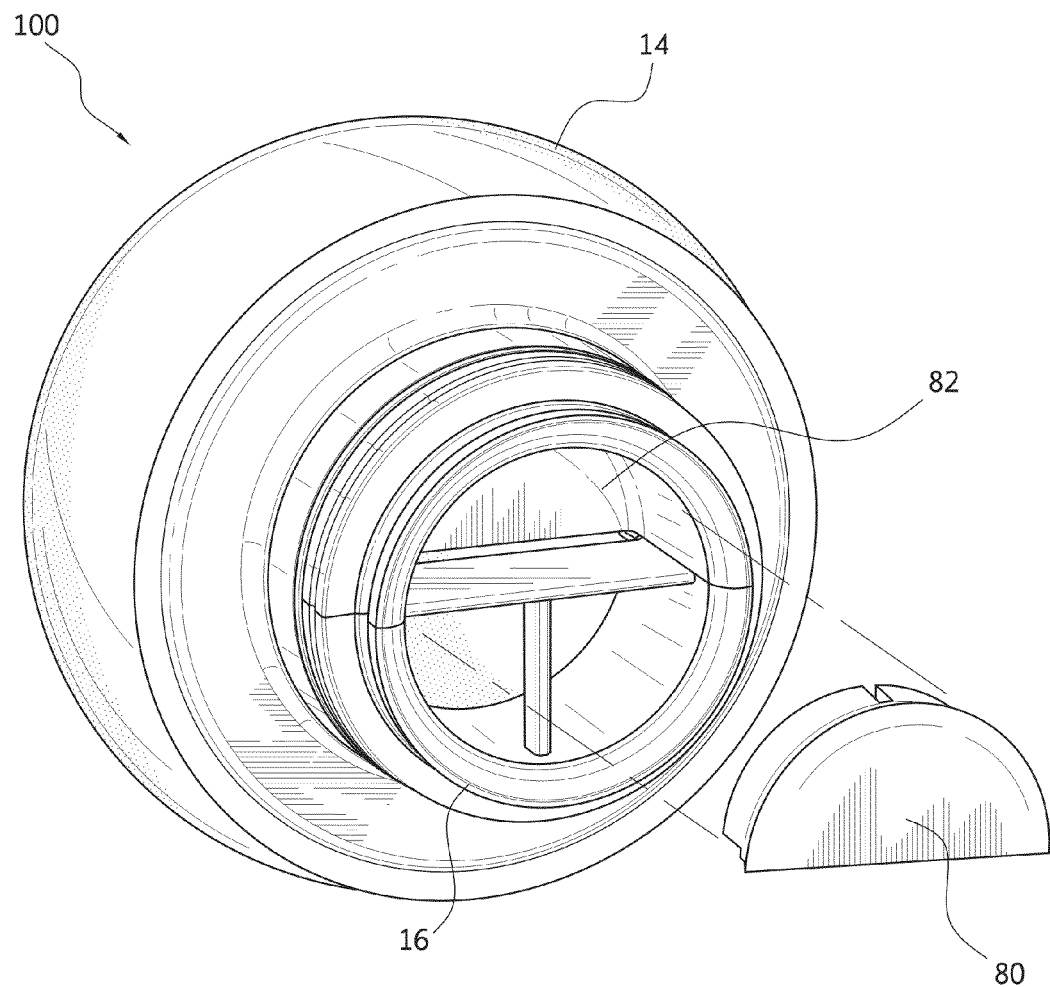
FIG. 5B is a perspective view of the lip enhancement and enlargement device shown in FIG. 5A, showing alignment of a blocking element with an upper cavity.
Figure 5C:
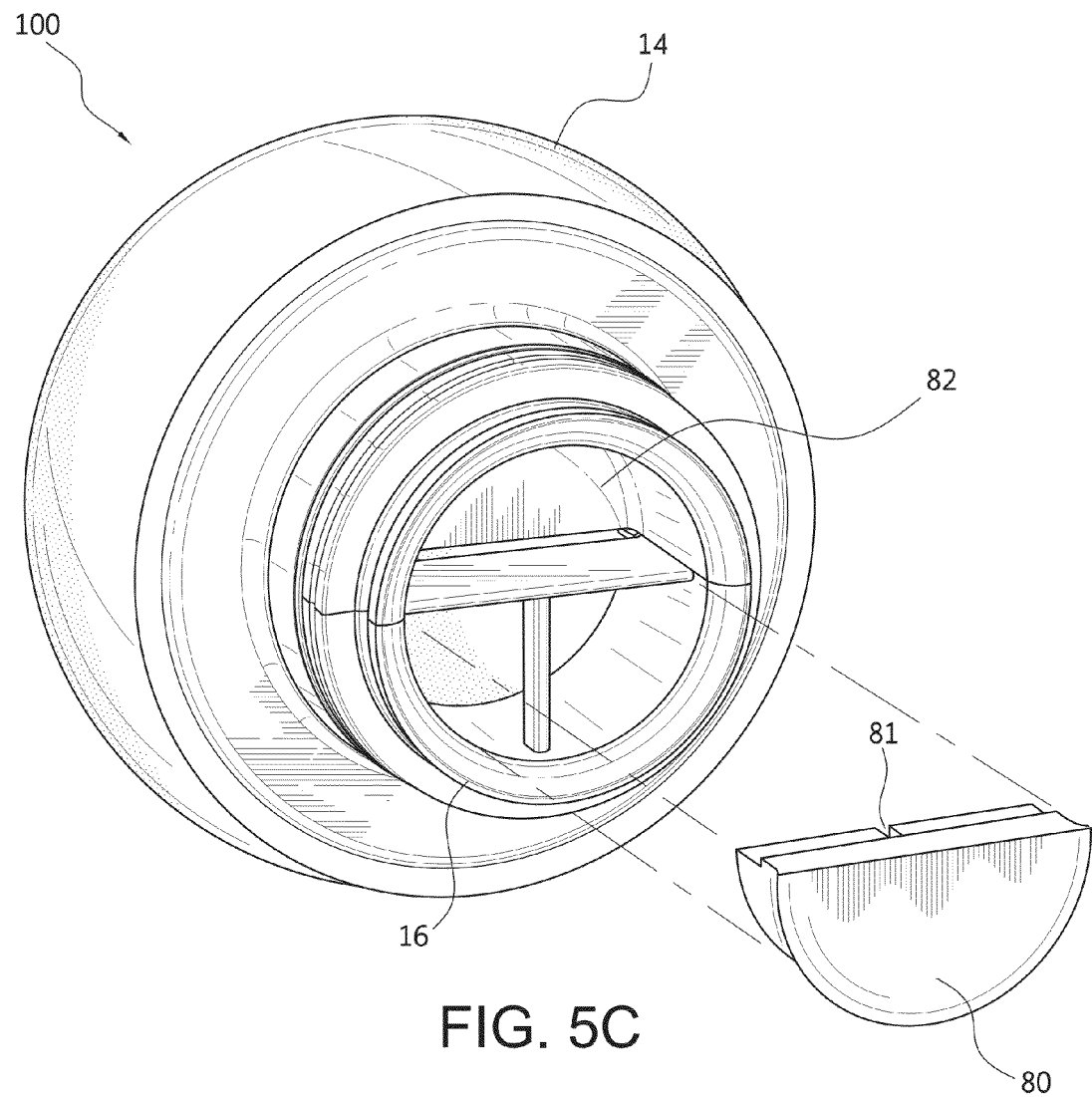
FIG. 5C is a perspective view of the lip enhancement and enlargement device shown in FIG. 5A, showing alignment of a blocking element with a lower cavity.
Figure 5D:
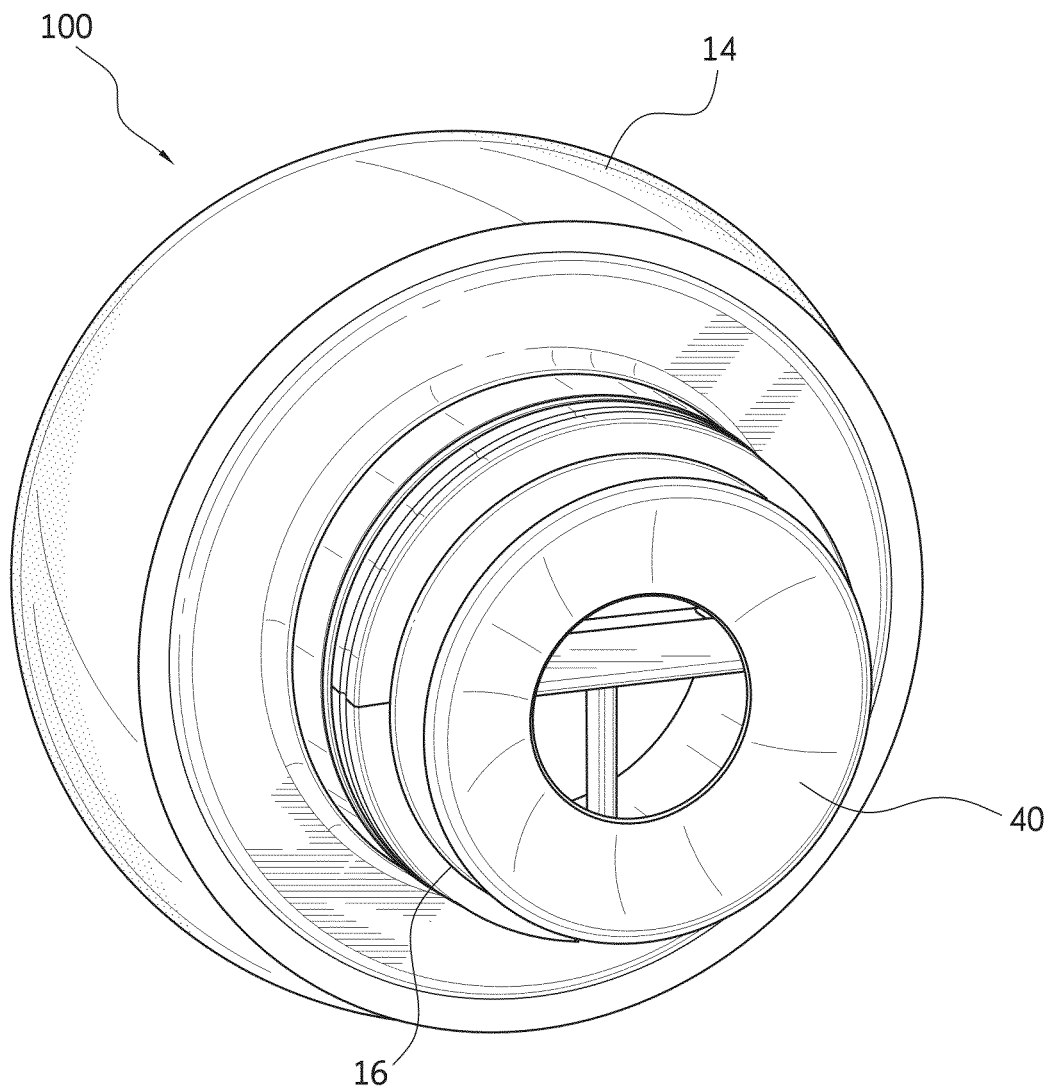
FIG. 5D is a perspective view of the upper section of the lip enhancement and enlargement device shown in FIG. 5A with a mark prevention element.
Figure 29A:
FIG. 29A is a front view of a user before application of a lip enhancement and enlargement device.
Figure 29B:
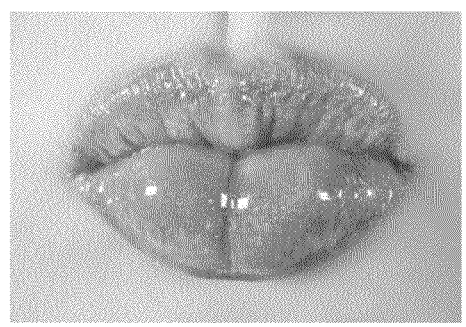
FIG. 29B is a front view of a user after application of a lip enhancement and enlargement device.

FIGS. 29A and 29B respectively, show before and after front views of the lips of a Female, Age: 44, who applied a lip enhancement and enlargement device 100 shown in FIG. 5B for approximately 4 minutes, where a blocker element was inserted into the upper lip shaper cavity.

Figure 30A:
FIG. 30A is a front view of a user before application of a lip enhancement and enlargement device.
Figure 30B:
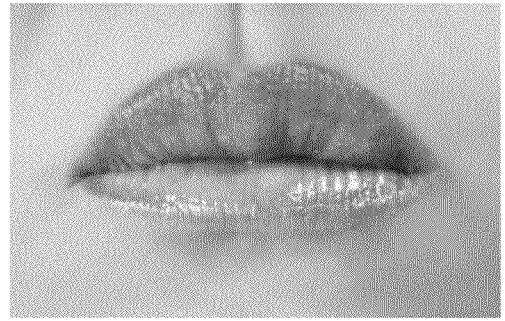
FIG. 30B is a front view of a user after application of a lip enhancement and enlargement device.

FIGS. 30A and 30B respectively, show before and after front views of the lips of a Female, Age: 44, who applied a lip enhancement and enlargement device 100 shown in FIG. 4B for approximately 4 minutes, where a blocker element was inserted into the lower lip shaper cavity.

Figure 31A:
FIG. 31A is a front view of a user before application of a lip enhancement and enlargement device.
Figure 31B:
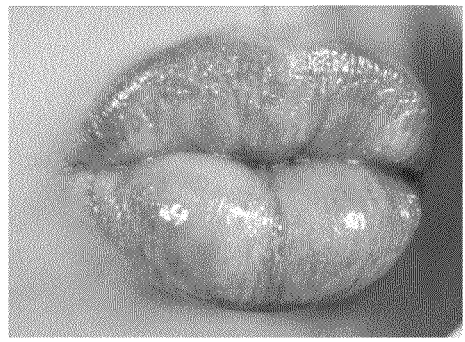
FIG. 31B is a front view of a user after application of a lip enhancement and enlargement device.

FIGS. 31A and 31B respectively, show before and after front views of the lips of a Female, Age: 44, who applied a lip enhancement and enlargement device 100 shown in FIG. 5A for approximately 6 minutes.

Figure 32A:
FIG. 32A is a front view of a user before application of a lip enhancement and enlargement device.
Figure 32B:
FIG. 32B is a front view of a user after application of a lip enhancement and enlargement device.

FIGS. 32A and 32B respectively, show before and after front views of the lips of a Female, Age: 44, who applied a lip enhancement and enlargement device 100 shown in FIG. 4B for approximately 4 minutes, where a blocker element was inserted into the upper lip shaper cavity.

Accordingly, lip enhancement and enlargement devices, kits, and methods are disclosed. While certain embodiments illustrating the present technology have been shown and described herein, it will be apparent to those skilled in the art that many more modifications are possible without departing from the scope of the present disclosure. All examples presented are representative and non-limiting. The invention, therefore, is not to be restricted except in the spirit of the following claims.

What is claimed is:

1. A lip enhancement and enlargement method, comprising:
    applying a lip enhancement and enlargement device having a lip shaper assembly coupled to a suction element to a face;
    creating a seal between the lip shaper assembly and the face around a surrounding lip area, wherein the lip shaper assembly is configured to enable selective blocking of suction to any selected one of an upper lip or a lower lip;
    applying suction to a selected one of the upper lip, lower lip, or both lips using the suction element and maintaining the vacuum for a period of time;
    breaking the seal from the surrounding lip area after the period of time is elapsed; and
    removing the lip enhancement and enlargement device from the surrounding lip area.

2. The method of claim 1, wherein applying suction comprises compressing a resilient bladder to evacuate air, and then releasing compression of the bladder.

3. The method of claim 1, further comprising placing a suction blocking piece into one of an upper portion or lower portion of the lip shaper assembly.

4. The method of claim 1, further comprising contouring the selected one of the upper lip, lower lip, or both lips using a creasing member coupled to the lip shaper assembly.

* * * * *